(12) United States Patent
Fujihara

(10) Patent No.: US 8,759,502 B2
(45) Date of Patent: Jun. 24, 2014

(54) PROTECTING GROUP FOR INDOLE GROUP, NUCLEIC ACID-SYNTHESIZING AMIDITE AND NUCLEIC ACID-SYNTHESIZING METHOD

(75) Inventor: Tsuyoshi Fujihara, Kawasaki (JP)

(73) Assignee: Apta Biosciences Ltd., Ledbury (GB)

( * ) Notice: Subject to any disclaimer, the term of this patent is extended or adjusted under 35 U.S.C. 154(b) by 658 days.

(21) Appl. No.: 12/950,836

(22) Filed: Nov. 19, 2010

(65) Prior Publication Data
US 2011/0118455 A1 May 19, 2011

(30) Foreign Application Priority Data
Nov. 17, 2009 (JP) ................................. 2009-262124

(51) Int. Cl.
C07H 21/02 (2006.01)
C07H 21/04 (2006.01)
C07H 19/04 (2006.01)
C07H 19/16 (2006.01)
C07H 19/23 (2006.01)
C07H 19/207 (2006.01)

(52) U.S. Cl.
USPC ...... 536/23.1; 536/26.1; 536/26.7; 536/26.72

(58) Field of Classification Search
USPC ............................. 536/23.1, 26.1, 26.7, 26.72
See application file for complete search history.

(56) References Cited

U.S. PATENT DOCUMENTS

| | | | |
|---|---|---|---|
| 6,605,708 B1 | 8/2003 | Habus et al. | |
| 7,759,473 B2 * | 7/2010 | Fujihara et al. | 536/23.1 |
| 2009/0053710 A1 | 2/2009 | Fujihara et al. | |
| 2009/0062521 A1 | 3/2009 | Fujihara | |
| 2010/0197902 A1 | 8/2010 | Fujihara | |

FOREIGN PATENT DOCUMENTS

| | | |
|---|---|---|
| JP | 9-503494 | 4/1997 |
| JP | 2008-230985 | 10/2008 |
| JP | 2009-62307 | 3/2009 |
| WO | WO 03/078623 A1 | 9/2003 |
| WO | WO 2009/028345 | 3/2009 |

OTHER PUBLICATIONS

Jarmo Heikkila et al., "The 9-Fluorenylmethoxycarbonyl (Fmoc) Group for the Protection of Amino Functions of Cytidine, Adenosine, Guanosine and Their 2'- Deoxysugar Derivatives", Acta Chemica Scandinavica, B37, 1983, No. 3, pp. 263-265.

Leo H. Koole et al., "Synthesis of Phosphate-Methylated NA Fragments Using 9-Fluorenylmethoxycarbonyl as Transient Base Protecting Group", J. Org. Chem., 1989, 54, pp. 1657-1664.

W.H.A. Kuijpers et al., "The application of the AMB protective group in the solid-phase synthesis of methylphosphonate DNA analogues", Nucleic Acids Research, 1993, vol. 21, No. 15, pp. 3493-3500.

Anna Maria Avino et al., "Use of NPE-Protecting Groups for the Preparation of Oligonucleotides Without Using Nucleophiles During the Final Deprotection", Nucleosides & Nucleotides, 1994, 13(10), pp. 2059-2069.

W.H.A. Kuijpers et al., "The 2-(Acetoxymethyl) Benzoyl (AMB) Group as a New Base-Protecting Group, Designed for the Protection of (Phosphate) Modified Oligonucleotides", Tetrahedron Letters, 1990, vol. 31, No. 46, pp. 6729-6732.

Ramon Eritja et al., "A Synthetic Procedure for the Preparation of Oligonucleotides Without Using Ammonia and Its Application for the Synthesis of Oligonucleotides Containing a O-4-Alkyl Thymidines", Tetrahedron Letters, 1992, vol. 48, No. 20, pp. 4171-4182.

Japanese Office Action issued Jan. 21, 2014, in corresponding Japanese Patent Application No. 2009-262124 (with English-language Translation).

Theodora W. Green et al., "Protective Groups in Organic Synthesis," Third Edition, p. 540, (1999), John Wiley & Sons, Inc.

* cited by examiner

*Primary Examiner* — Yong Chu
(74) *Attorney, Agent, or Firm* — Oblon, Spivak, McClelland, Maier & Neustadt, L.L.P.

(57) ABSTRACT

A protecting group for 1-nitrogen atom of an indole group including a sulfonylethyl carbamate group, wherein the protecting group is represented by the following General Formula (I) and capable of being removed from the 1-nitrogen atom of the indole group in an aprotic solvent:

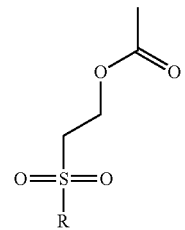

General Formula (I)

where R represents an alkyl group, a derivative of the alkyl group, a phenyl group or a derivative of the phenyl group.

10 Claims, 14 Drawing Sheets

US 8,759,502 B2

PROTECTING GROUP FOR INDOLE GROUP, NUCLEIC ACID-SYNTHESIZING AMIDITE AND NUCLEIC ACID-SYNTHESIZING METHOD

CROSS-REFERENCE TO RELATED APPLICATION

This application is based upon and claims the benefit of the priority of the prior Japanese Patent Application No. 2009-262124, filed on Nov. 17, 2009, the entire contents of which are incorporated herein by reference.

FIELD

The embodiments discussed herein relate to a protecting group for 1-nitrogen atom of an indole group, a nucleic acid-synthesizing amidite suitable for the production of a nucleic acid, a precursor of the nucleic acid-synthesizing amidite, a nucleic acid-synthesizing method using the nucleic acid-synthesizing amidite, and a nucleic acid synthesized by the nucleic acid-synthesizing method.

BACKGROUND

Unraveling of the whole human genome has shifted the focus of interest of scientists and researchers on the analysis of proteins; i.e., gene products. It may not be overstating to say that substantial protein analysis can be made possible only when a molecule that exhibits affinity (binding property) for each protein of interest has been successfully obtained. Cells, however, each contain quite many different types of proteins, and the amino acid sequence and structure of many of which are still unknown.

The most common technique for obtaining a molecule that exhibits affinity for a specific protein is to prepare an affinity antibody by utilizing the immune system of animal. However, this technique uses animals and thus, requires a large quantity of proteins, a large number of steps and large cost. Additionally, no affinity antibody can be obtained for specific substances with this technique. A technique called the aptamer method (also referred to as the SELEX method) that does not rely on any living organism has been proposed to avoid this problem. However, while a molecule obtained by this technique strongly interacts with a specific protein, this technique is not applicable to all the proteins.

In view of such circumstances, the present inventors proposed a modified aptamer method that is established by improving the aptamer method so as to use nucleic acids (see International Publication No. WO 2003/078623). However, since the modified aptamer method uses a number of different modified nucleic acids, and thus, it has been difficult to find appropriate PCR conditions. Additionally, the above method poses a problem that a functional molecule that tends to be strongly bound to a target substance is hard to be amplified by PCR. In order to solve the above existing problems, the present inventors have previously proposed a method for synthesizing an amidite (raw material) of a functional molecule in which the functional groups participating in binding to the target substance correspond one-to-one to the sequences of the dimers, and the functional groups are removed after binding to proteins and then, the resultant product can be amplified by PCR.

Meanwhile, a solid-phase synthesis of nucleic acids has been performed for 20 years or longer, and an automated synthesizer employing it was also sold at that time. The solid-phase synthesis of nucleic acids is performed by, for example, condensating nucleoside compounds (amidites) with nucleosides bound to a solid-phase support (e.g., CPG). During this condensation reaction, it is necessary that only the phosphoric acid moiety of each amidite is condensed with only the hydroxyl group of another amidite so that the other reactive groups do not participate in the condensation reaction. Thus, protecting groups are introduced to the reactive groups (e.g., exocyclic amino groups of nucleic acid bases of amidites used and a phosphoric acid moiety which is not made to participate in the condensation reaction) so that they do not participate in the condensation reaction, and the protecting groups are removed (deprotected) after completion of the whole condensation reaction. Conventionally, a benzoyl group, an isobutyryl group, other groups have been used as a protecting group which is introduced to the exocyclic amino group of a nucleic acid base, and these protecting groups are generally removed by treating the obtained nucleic acid with concentrated aqueous ammonia at 55° C. for 8 hours to 15 hours.

However, in the production of nucleic acids having affinity (binding property) for proteins, under such conventional deprotection conditions, not only the protecting groups but also their modified moieties (substituents having binding property for proteins) are removed, resulting in that modified nucleic acids cannot be stably produced. Thus, in the production of such modified nucleic acids, in order to prevent the substituents having binding property for proteins from being removed together with the protecting groups, there is a need to use amidites having protecting groups which is capable of being removed under milder conditions.

For example, some conventional literatures report nucleic acid amidites having protecting groups which is capable of being removed by diazabicycloundecene (DBU) (i.e., a bulky base) (Acta. Chem., Scand., B37, 263 (1983) and J. Org. Chem., 54, 1,657 (1989)). But, these nucleic acid-synthesizing amidites are not stable in acetonitrile (i.e., an aprotic solvent) (Tetrahedron Letters 46, 6,729 (1990)) and are not suitable to practical use. Other literatures report nucleic acid-synthesizing amidites having protecting groups which is capable of being removed in pyridine using 0.5M DBU for 16 hours (Tetrahedron 48, 4,171 (1992) and Nucleosides & Nucleotides 13, 2,059 (1994)). But, the use of a high concentration of DBU and the deprotection for a long time problematically cause alkylation of the base of nucleic acid. Other literatures report nucleic acid-synthesizing amidites having protecting groups which is capable of being removed in methanol using $K_2CO_3$ (Tetrahedron Letters 46, 6,729 (1990) and Nucleic Acids Research 21, 3,493 (1993)). But, use of $K_2CO_3$ (a base) in methanol (a protic solvent) problematically causes decomposition of the esters, etc.

Therefore, demand has arisen for the developments of an excellent protecting group which is capable of being removed under mild conditions and with which a nucleic acid suitable for the analyses of target substances (e.g., proteins) can be consistently produced; a nucleic acid-synthesizing amidite having such protecting group; and a nucleic acid-synthesizing method using the nucleic acid-synthesizing amidite.

SUMMARY

According to an aspect of an embodiment, a protecting group for 1-nitrogen atom of an indole group includes at least a sulfonylethyl carbamate group, as shown in the below-given General Formula (I).

According to another aspect of an embodiment, a nucleic acid-synthesizing amidite includes at least a nucleic acid base, an indole group, and a protecting group for 1-nitrogen atom of the indole group, as shown in the below-given General Formulas (II) and (III).

According to still another aspect of an embodiment, a precursor of a nucleic acid-synthesizing amidite is that of the above nucleic acid-synthesizing amidite and has any one of Structural Formulas (3) to (7).

According to yet another aspect of an embodiment, a nucleic acid-synthesizing method uses the above nucleic acid-synthesizing amidite.

According to even another aspect of an embodiment, a nucleic acid is obtained by the above nucleic acid-synthesizing method. Thus, the above nucleic acid has an indole group.

The object and advantages of the invention will be realized and attained by means of the elements and combinations particularly pointed out in the claims. It is to be understood that both the foregoing general description and the following detailed description are exemplary and explanatory and are not restrictive of the invention, as claimed.

BRIEF DESCRIPTION OF DRAWINGS

FIG. 4-1 is a $^1$H-NMR spectrum of a nucleic acid-synthesizing amidite having Structural Formula (1) and obtained in Example 1;
FIG. 4-2 is a $^{31}$P-NMR spectrum of a nucleic acid-synthesizing amidite having Structural Formula (1) and obtained in Example 1;
FIG. 7-1 is a $^1$H-NMR spectrum of a nucleic acid-synthesizing amidite having Structural Formula (2) and obtained in Example 1;
FIG. 7-2 is a $^{31}$P-NMR spectrum of a nucleic acid-synthesizing amidite having Structural Formula (2) and obtained in Example 1;
FIG. 7-3 is an HH cosy spectrum of a nucleic acid-synthesizing amidite having Structural Formula (2) and obtained in Example 1.

Figure 1:
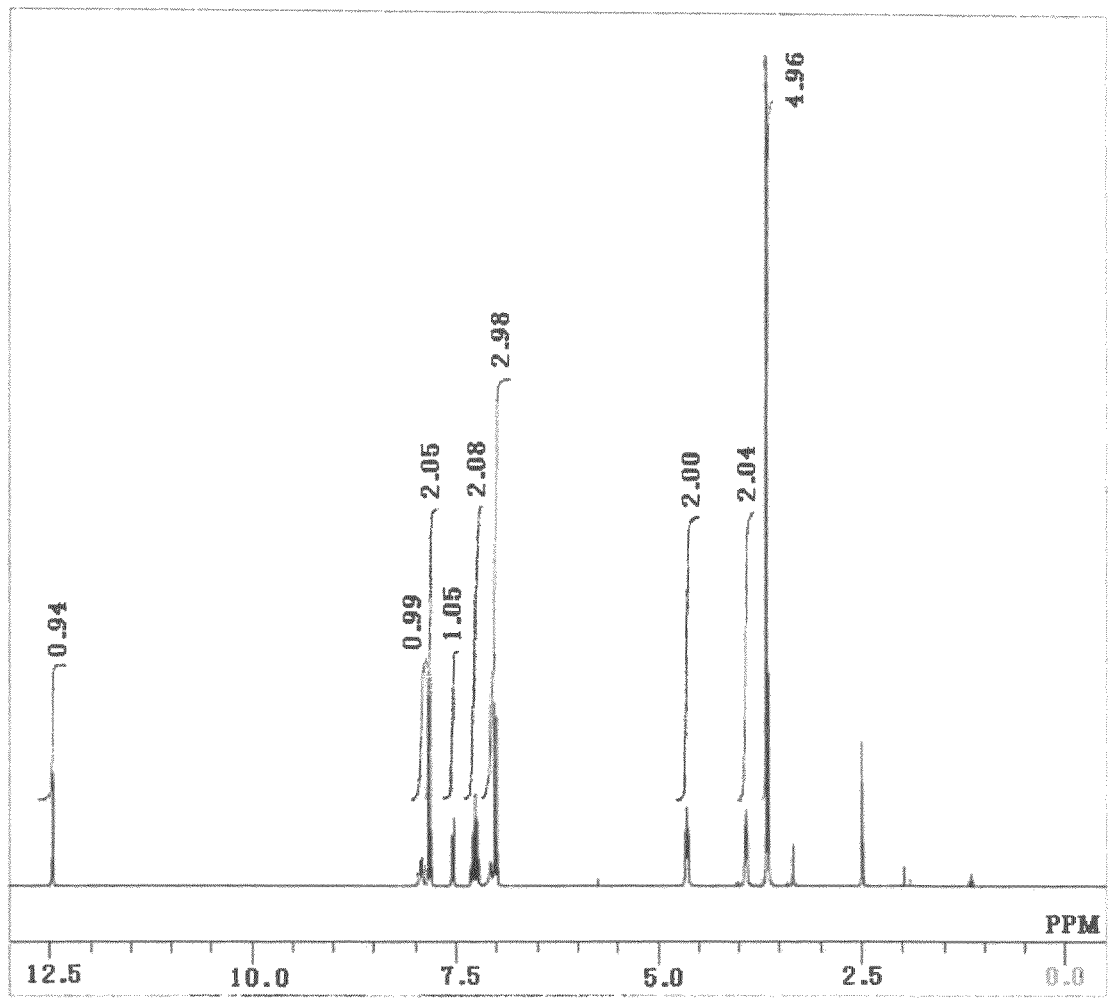
FIG. 1 is a $^1$H-NMR spectrum of a compound having Structural Formula (3) and obtained in Example 1.
Figure 2:
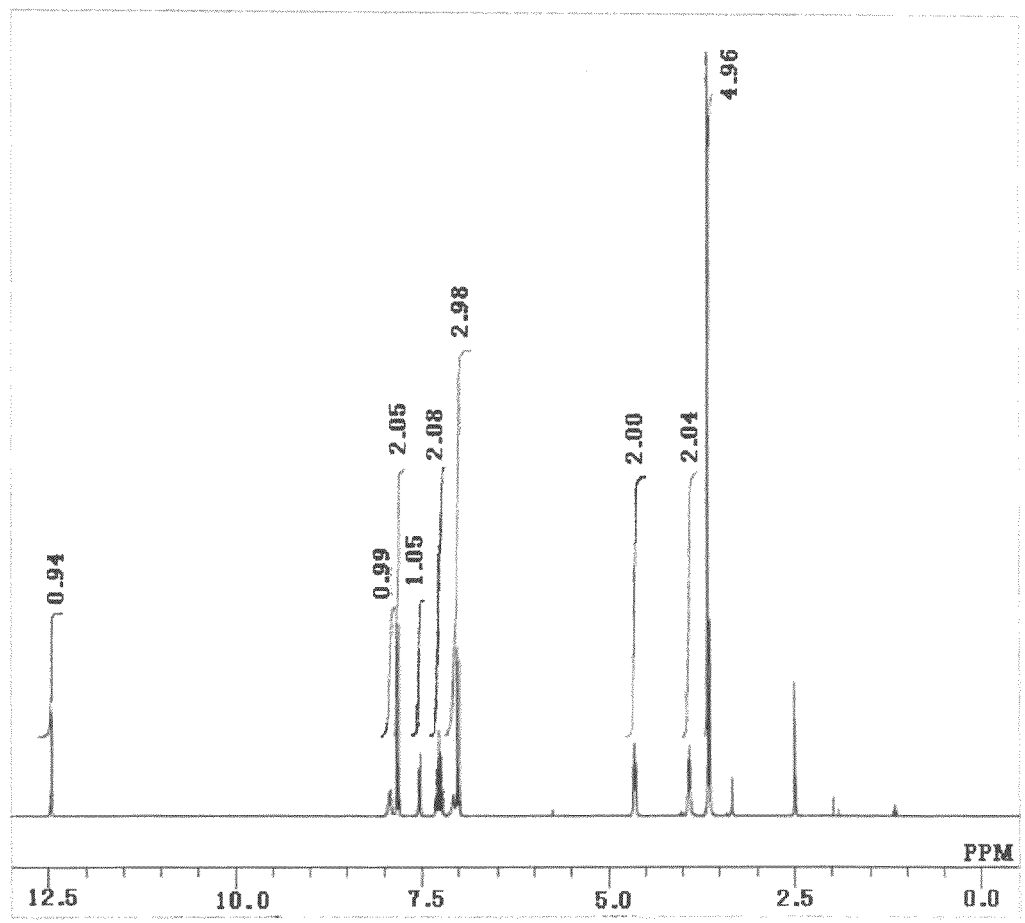
FIG. 2 is a $^1$H-NMR spectrum of a compound having Structural Formula (4) and obtained in Example 1.
Figure 3:
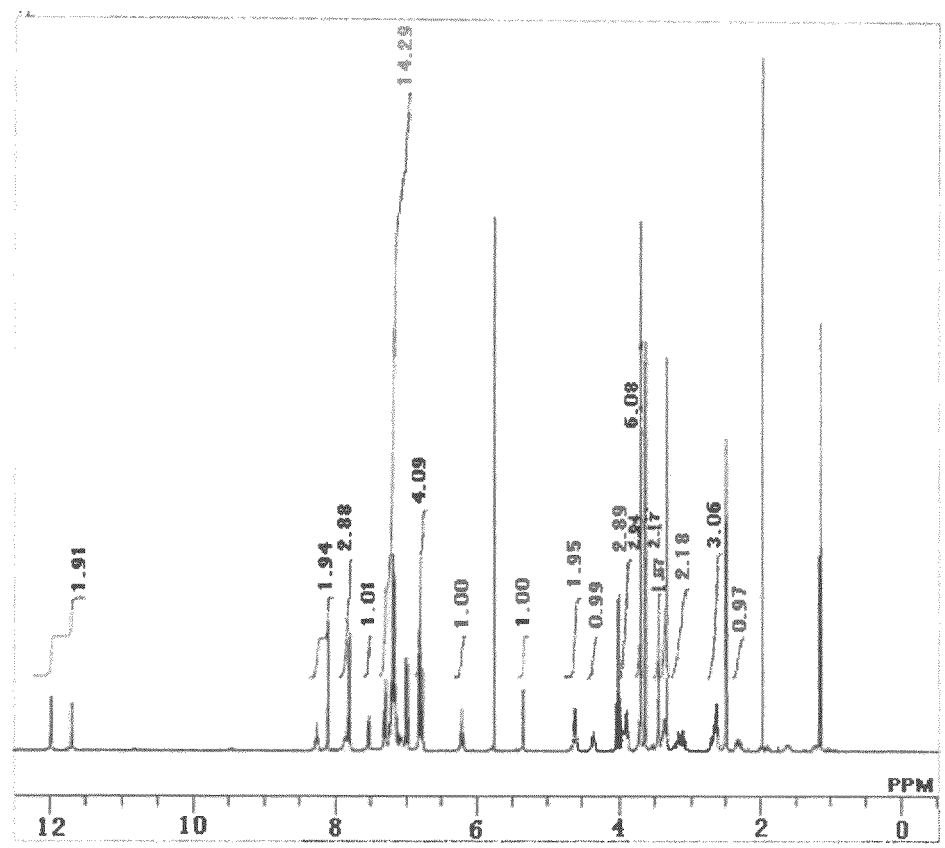
FIG. 3 is a $^1$H-NMR spectrum of a compound having Structural Formula (5) and obtained in Example 1.
Figures 1, 4:
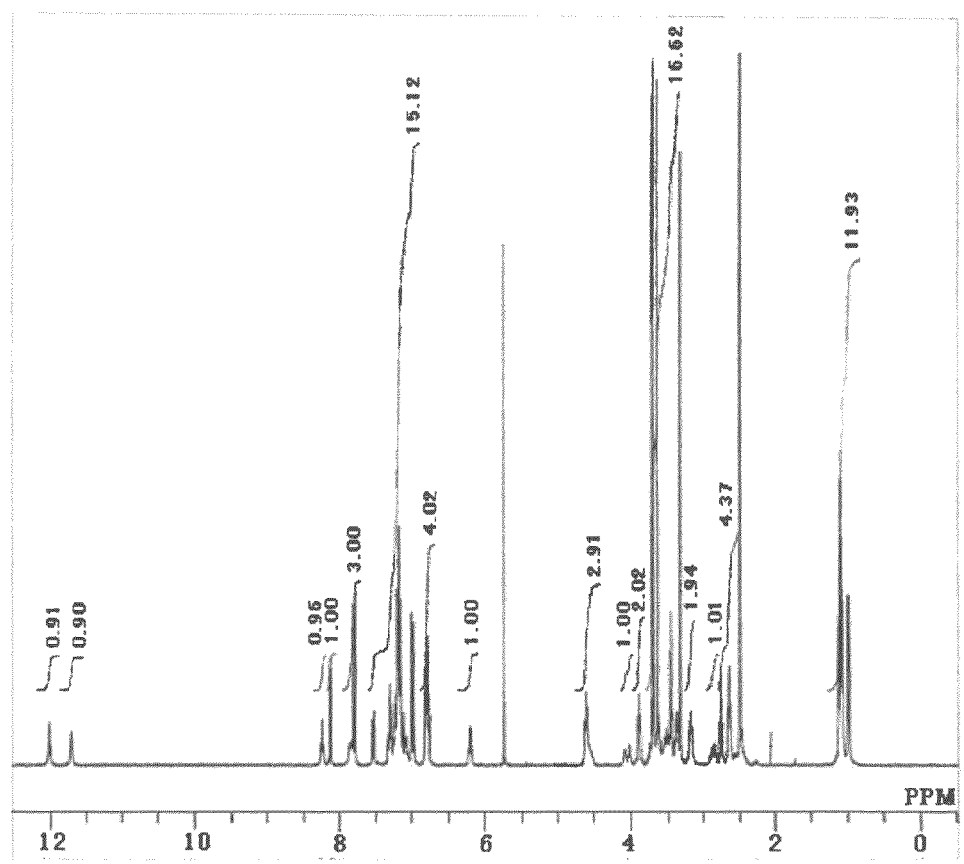
Figures 2, 4:
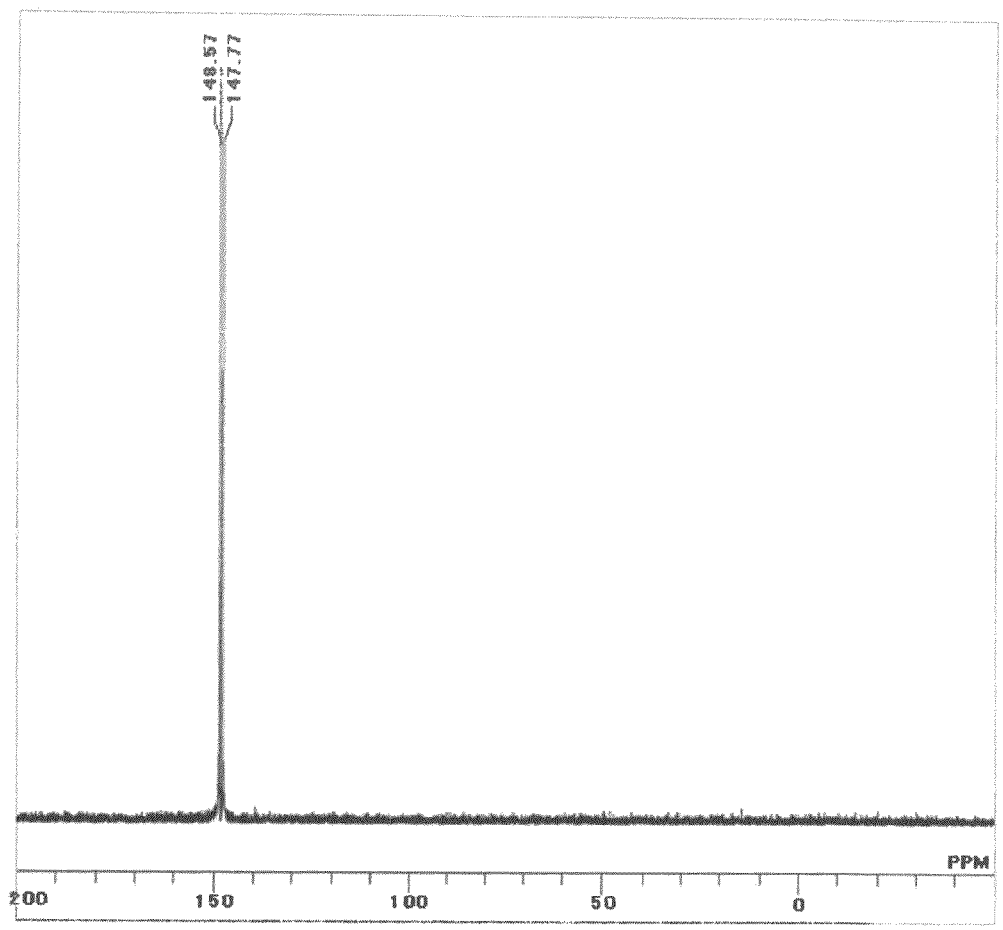
Figure 5:
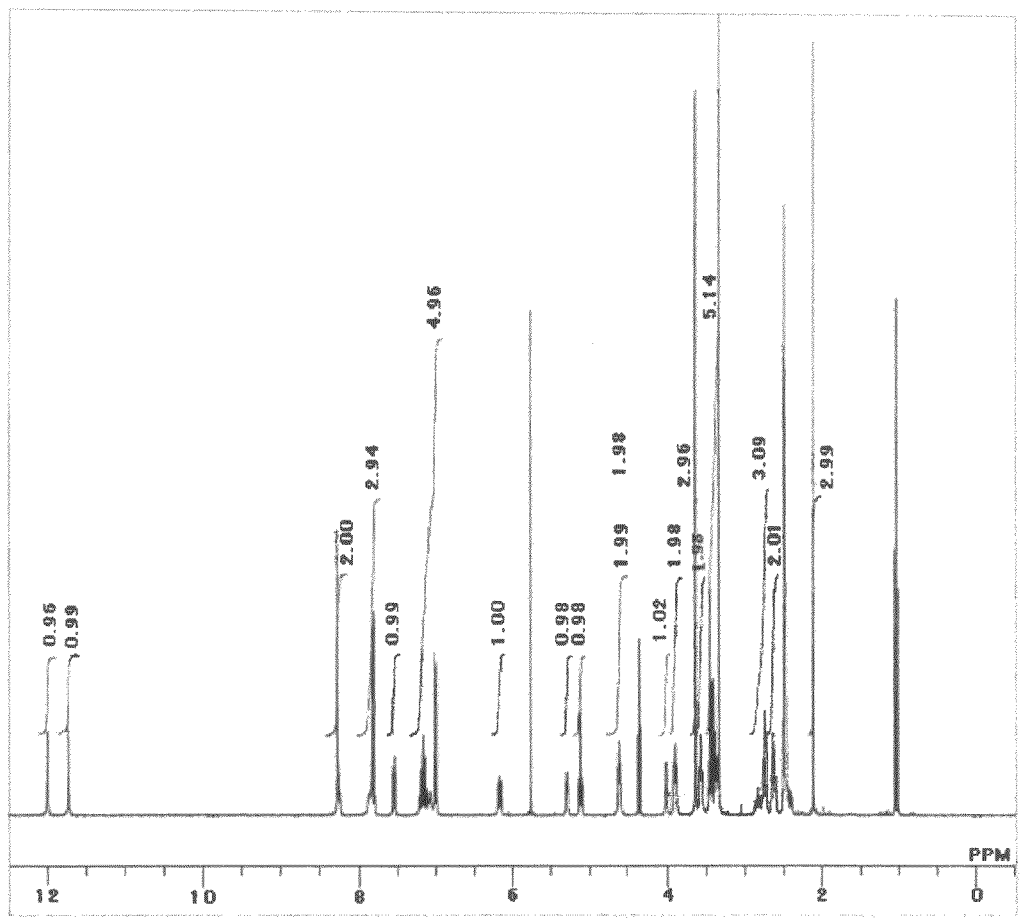
FIG. 5 is a $^1$H-NMR spectrum of a compound having Structural Formula (6) and obtained in Example 1.
Figure 6:
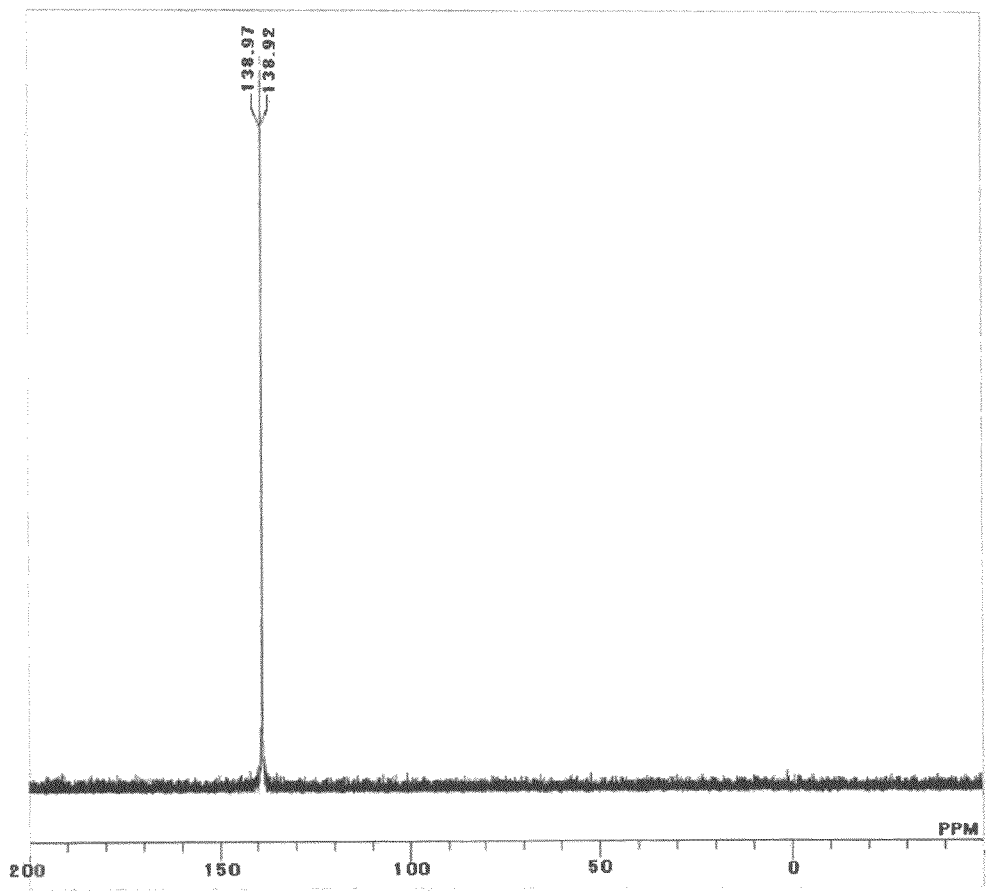
FIG. 6 is a $^{31}$P-NMR spectrum of a compound having Structural Formula (7) and obtained in Example 1.
Figures 1, 7:
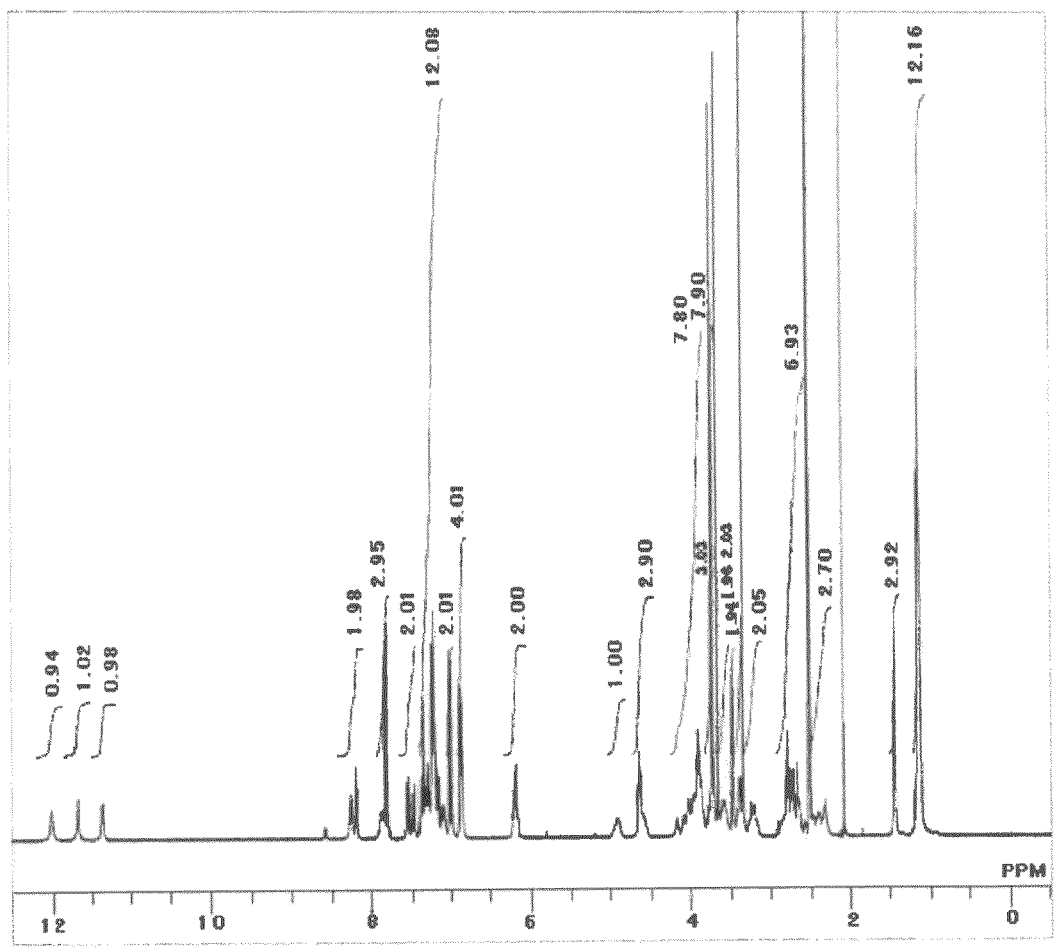
Figures 2, 7:
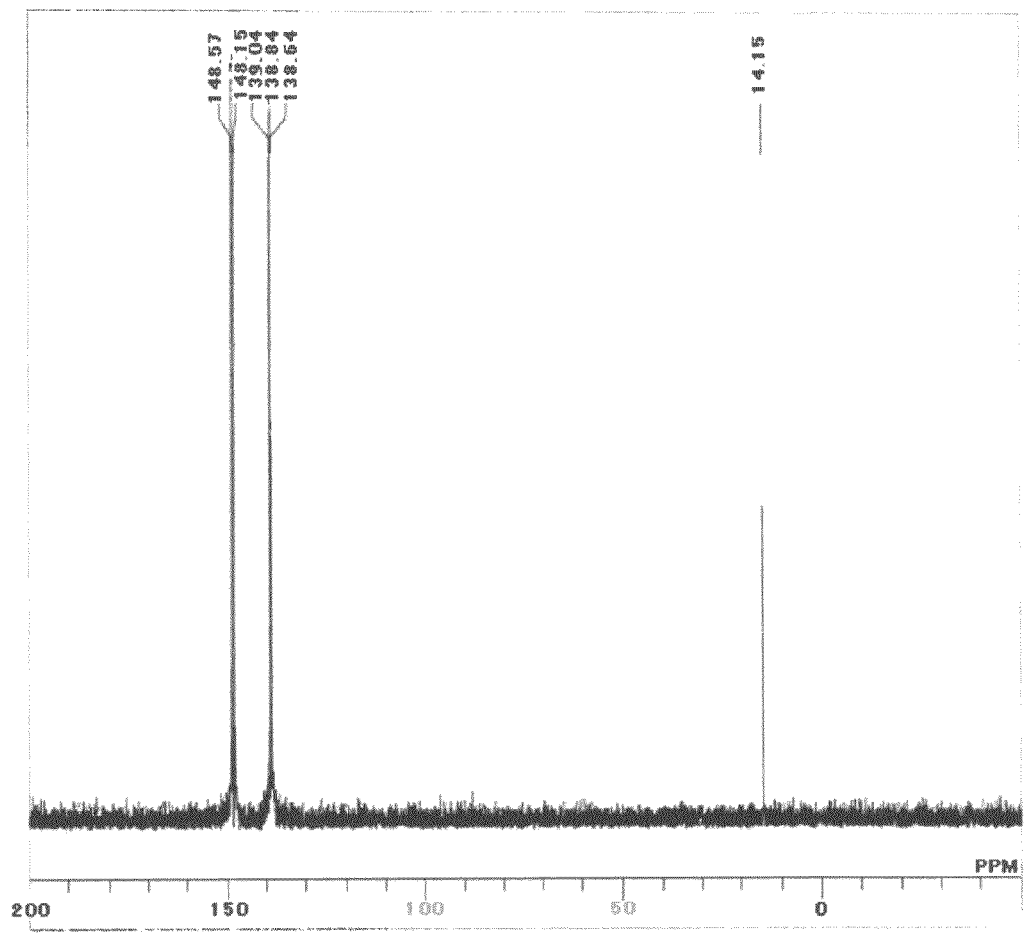
Figures 3, 7:
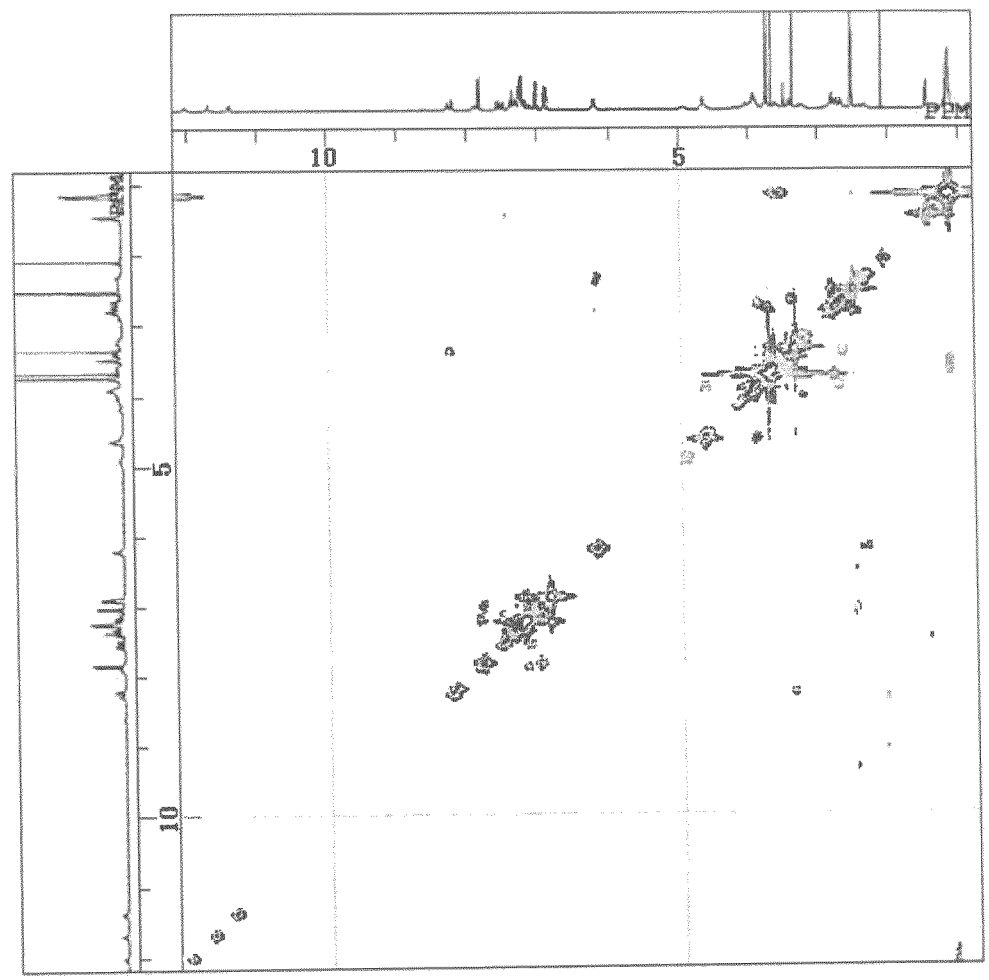

DESCRIPTION OF EMBODIMENTS (Protecting group for 1-nitrogen atom of an indole group (indole group-protecting group)) The indole group-protecting group is a protecting group for 1-nitrogen atom of an indole group, and includes a sulfonylethyl carbamate group and is represented by the following General Formula (I);

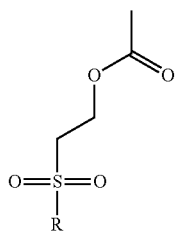

General Formula (I)

In General Formula (I), R represents an alkyl group, a derivative of the alkyl group, a phenyl group or a derivative of the phenyl group.

Also, the indole group to be protected is preferably an indole group modified at position 3 thereof.

The alkyl group is not particularly limited and may be appropriately selected depending on the intended purpose. Examples thereof include a methyl group.

The derivative of the phenyl group is not particularly limited and may be appropriately selected depending on the intended purpose. Examples thereof include an alkoxyphenyl group. The alkoxyphenyl group is not particularly limited and may be appropriately selected depending on the intended purpose. The alkoxyphenyl group is preferably a p-methoxyphenyl group.

The indole group-protecting group is a protecting group which is capable of being removed in an aprotic solvent; i.e., which is capable of being removed under mild conditions.

Here, the "protecting group which is capable of being removed under mild conditions" refers to a protecting group which is capable of being removed in an aprotic solvent by a bulky base.

The aprotic solvent is not particularly limited and may be appropriately selected depending on the intended purpose. Examples thereof include acetonitrile, dichloromethane, N,N-dimethylformamide (DMF) and N-methylpyrrolidone. Of these, when the indole group-protecting group is removed with a DNA synthesizer, acetonitrile is preferably used.

Since the indole group is not removed in the aprotic solvent from the nucleic acid base or amidite upon the removal of the indole group-protecting group, an indole group-containing nucleic acid can be produced consistently.

The bulky base is not particularly limited, so long as it is a Lewis base or a Bronsted-Lowry base, and may be appropriately selected depending on the intended purpose. Examples thereof include 1,8-diazabicyclo[5.4.0]-7-undecene (DBU), 1,5-diazabicyclo[4.3.0]-5-nonene (DBN) and tetramethylguanidine. In particular, the indole group-protecting group is preferably removed in acetonitrile by DBU.

The concentration of DBU required for removing the protecting group is not particularly limited and may be appropriately determined depending on the intended purpose. The concentration of DBU is preferably 0.5M or lower, more preferably 0.1M or lower, particularly preferably 0.01M or lower.

The indole group-protecting group is preferably removed so that the concentrations of the by-products removed and DBU are not be increased. Specifically, by applying a DBU-containing solution to a solid-phase support having synthesized DNA fragments fixed thereon, the DNA fragments and the by-products are physically separated from each other so that the DNA fragments remain on the solid-phase support and the by-products transfer to the solution.

When the reaction mixture is concentrated without separating the DBU, by-products and DNA fragments, and the concentration of DBU exceeds 0.5M, the nucleic acid base may be alkylated.

The time required for the removal of the protecting group is not particularly limited and may be appropriately determined depending on the intended purpose. The required time is preferably 8 hours or shorter, more preferably 1 hour or shorter, particularly preferably 15 minutes or shorter.

When the time required for the removal of the protecting group exceeds 8 hours without separating the by-products, the nucleic acid base may be alkylated.

The sulfonylethyl carbamate group of the indole group-protecting group is unstable under basic conditions, and the indole group-protecting group is removed by a bulky base in the aprotic solvent. Meanwhile, the indole group-protecting group is also preferably introduced into the indole group under basic conditions. Therefore, preferably, a thioethyl carbamate group stable under basic conditions is introduced into the indole group, and then, oxidized to the sulfonylethyl carbamate group.

The indole group-protecting group can be suitably used for the synthesis of indole group-containing nucleic acid. The indole group-protecting group is capable of being removed under mild conditions. Thus, the protecting group can be easily removed without removing the indole group from the nucleic acid base or amidite.

(Nucleic acid-synthesizing amidite) The nucleic acid-synthesizing amidite contains an indole group whose 1-nitrogen atom is protected by a protecting group which is capable of being removed from the 1-nitrogen atom of the indole group in an aprotic solvent, and is represented by at least one of the following General Formulas (II) and (III):

General Formula (II)

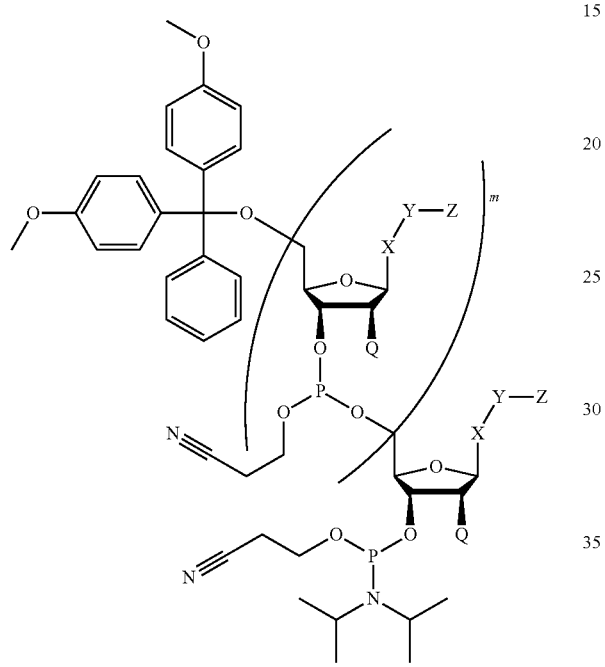

General Formula (III)

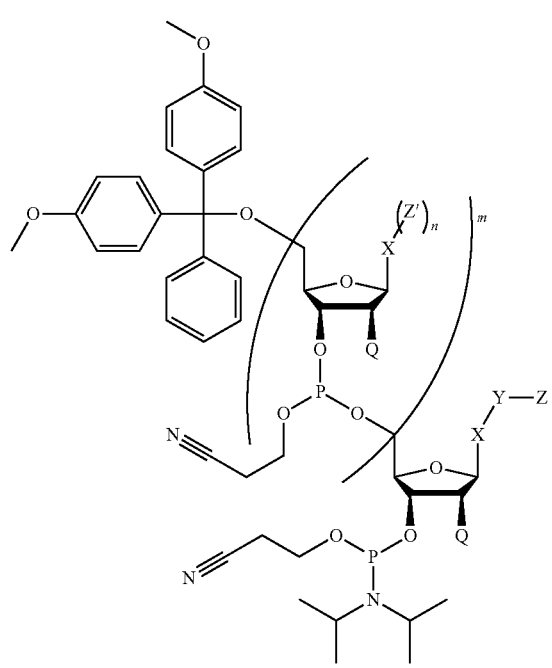

In General Formulas (II) and (III), X represents a nucleic acid base which may have a substituent, Y represents the indole group, Z represents the protecting group for the 1-nitrogen atom of the indole group, Z' represents a protecting group for the nucleic acid base, Q represents a hydrogen atom or a hydroxyl group, and each of n and m is 0 or 1.

General Formula (II) or (III) where m is 0 represents a monomer of the nucleic acid-synthesizing amidite.

General Formula (II) or (III) where m is 1 represents a dimer of the nucleic acid-synthesizing amidite. In the dimer of the nucleic acid-synthesizing amidite, at least one monomer of the nucleic acid-synthesizing amidite may contain the indole group Y. As shown in General Formula (III), one nucleic acid-synthesizing amidite may contain only the nucleic acid base X or the protecting group Z'-containing nucleic acid base X. Further, the dimer of the nucleic acid-synthesizing amidite may be those represented by the following General Formula (IV):

General Formula (IV)

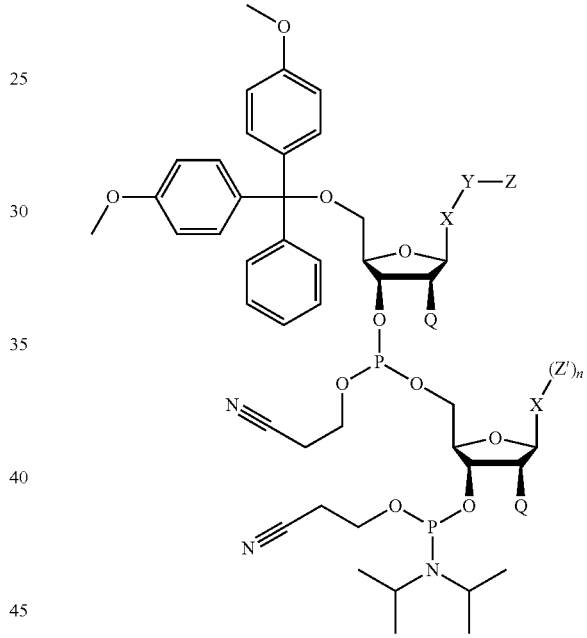

where X represents a nucleic acid base which may have a substituent, Y represents the indole group, Z represents the protecting group for the 1-nitrogen atom of the indole group, Z' represents a protecting group for the nucleic acid base, Q represents a hydrogen atom or a hydroxyl group, and n is 0 or 1.

<Indole group> The indole group represented by Y in General Formulas (II), (III) and (IV) is preferably introduced into the nucleic acid base represented by X in General Formulas (II), (III) and (IV) so that the indole group Y is not removed when the indole group-protecting group Z is removed under mild conditions.

The indole group may be bonded directly to the nucleic acid base X in General Formulas (II), (III) and (IV), or may be bonded to the nucleic acid base X via the below-described substituent the nucleic acid base has.

<Protecting group for indole group> In General Formulas (II), (III) and (IV), the protecting group Z is a protecting group for the 1-nitrogen atom of the indole group Y. The type of the protecting group is not particularly limited, so long as the protecting group is capable of being removed in an aprotic solvent; i.e., under mild conditions, and may be appropriately determined depending on the intended purpose. The protecting group is preferably the above indole group-protecting group represented by General Formula (I). In particular, the protecting group is preferably the indole group-protecting group represented by General Formula (I) where R is an alkoxyphenyl group. More preferably, R is a p-methoxyphenyl group from the viewpoint of increasing the yield of the nucleic acid-synthesizing amidite.

<Nucleic acid base> The nucleic acid base represented by X in General Formulas (II), (III) and (IV) is not particularly limited and may be appropriately selected depending on the intended purpose. Examples thereof include adeninyl (A), guaninyl (G), cytosinyl (C), thyminyl (T) and uracilyl (U), with adeninyl (A), guaninyl (G), cytosinyl (C) and uracilyl (U) being preferred.

Also, the nucleic acid base X is not particularly limited, so long as it has a nucleic acid base, and may be appropriately selected depending on the intended purpose. The nucleic acid base X may be, for example, the below-described nucleoside compounds. Also, the nucleic acid base may have a substituent.

Further, in the nucleic acid-synthesizing amidite represented by General Formula (III) or (IV), the nucleic acid base X may have the protecting group Z' for the nucleic acid base. In General Formulas (III) and (IV), when the number of the protecting group Z' is 0; i.e., the nucleic acid base has no protecting group Z', the nucleic acid base X is a saturated nucleic acid base (not having any substituent).

The position at which the indole group Y or substituent is introduced to the nucleic acid base X is not particularly limited and may be appropriately selected depending on the intended purpose. For example, the position is preferably the 6-position of the adenine base, the 6-position of the cytosine base and the 2-position of the guanine base.

<<Nucleoside compound>> The "nucleoside compound" refers to a monomer of nucleoside or a nucleoside derivative used for the synthesis of nucleic acid. The nucleoside derivative encompasses a "nucleic acid synthesizing amidite" whose end has been modified so as to serve as an amidite.

The nucleoside compounds may be, for example, amidites having the following Structural Formulas described in, for example, JP-A Nos. 2008-162992, 2008-230985 and 2009-062307. In addition, there can be employed amidites having a protecting group only at the site where the phosphoric acid is bonded, such as cyanine dye amidites and commercially available dT amidites.

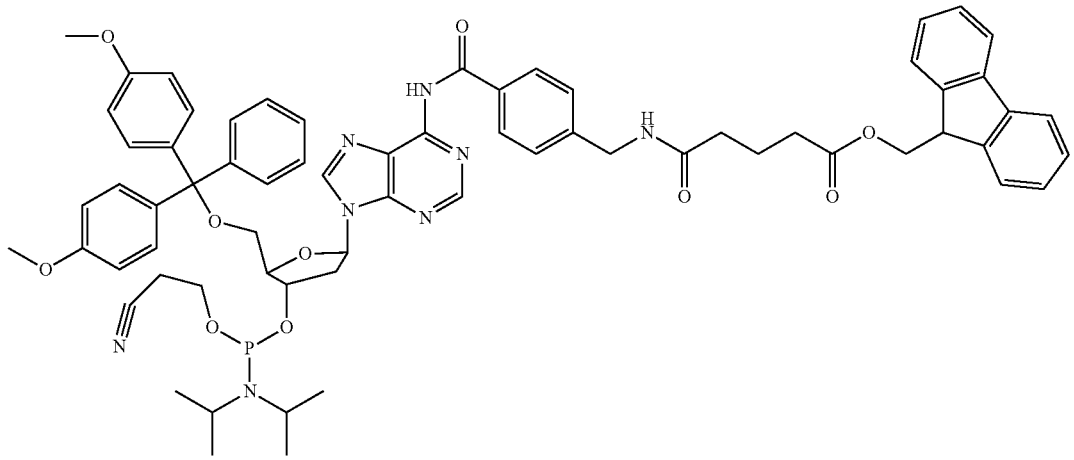

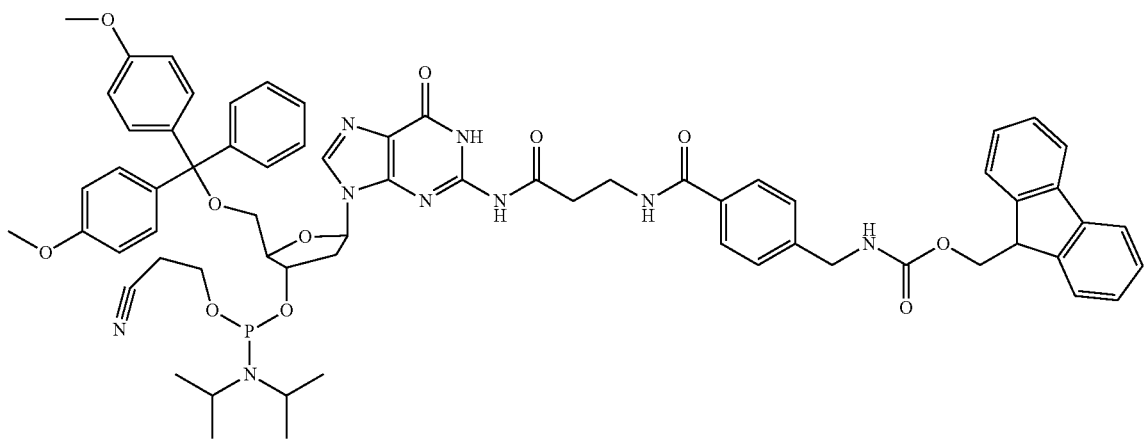

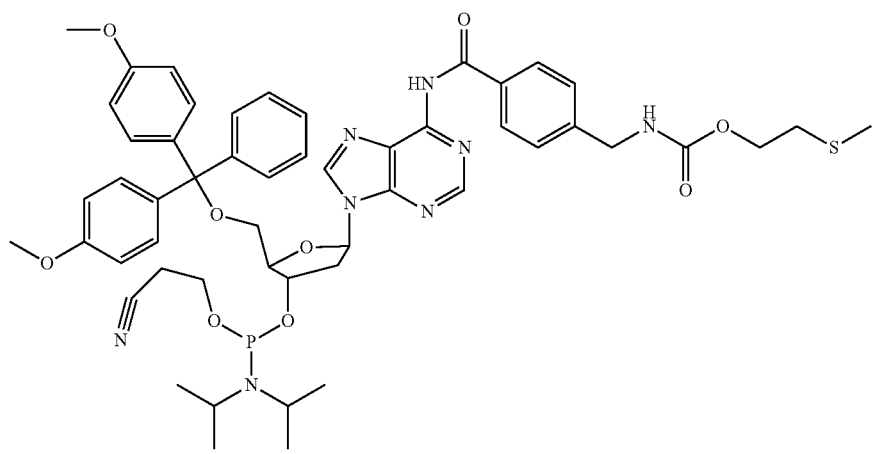
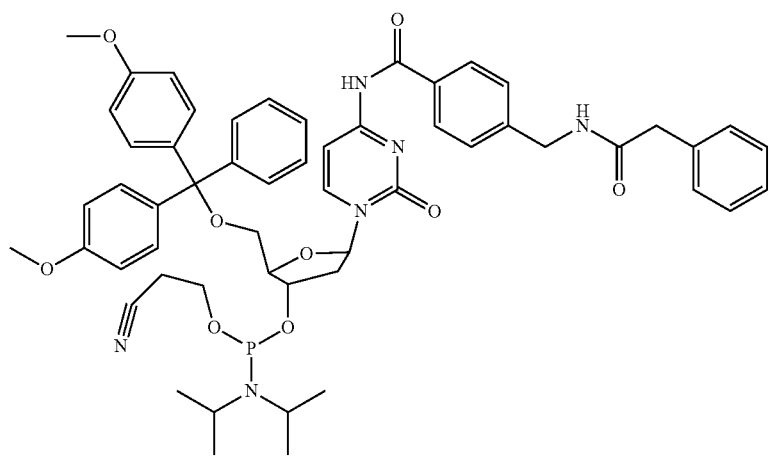
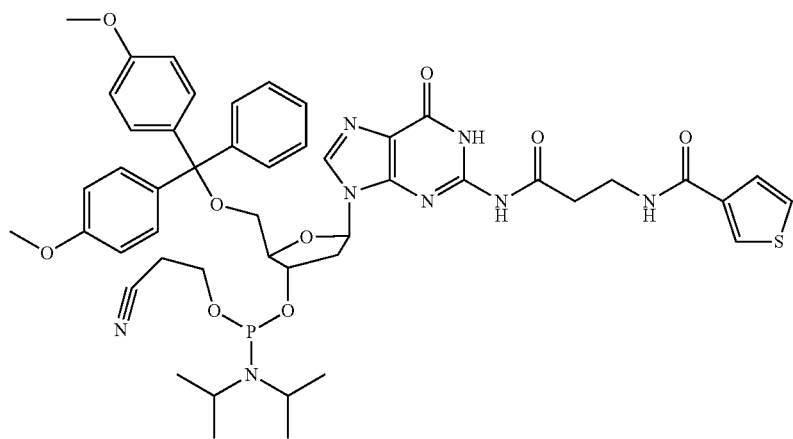

11
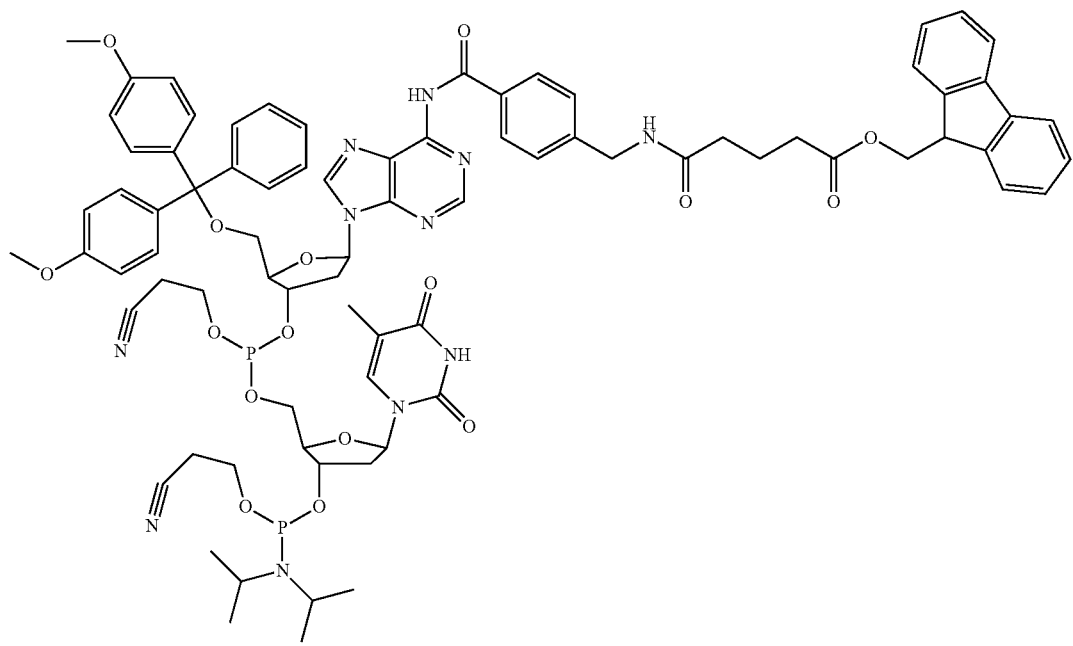
12
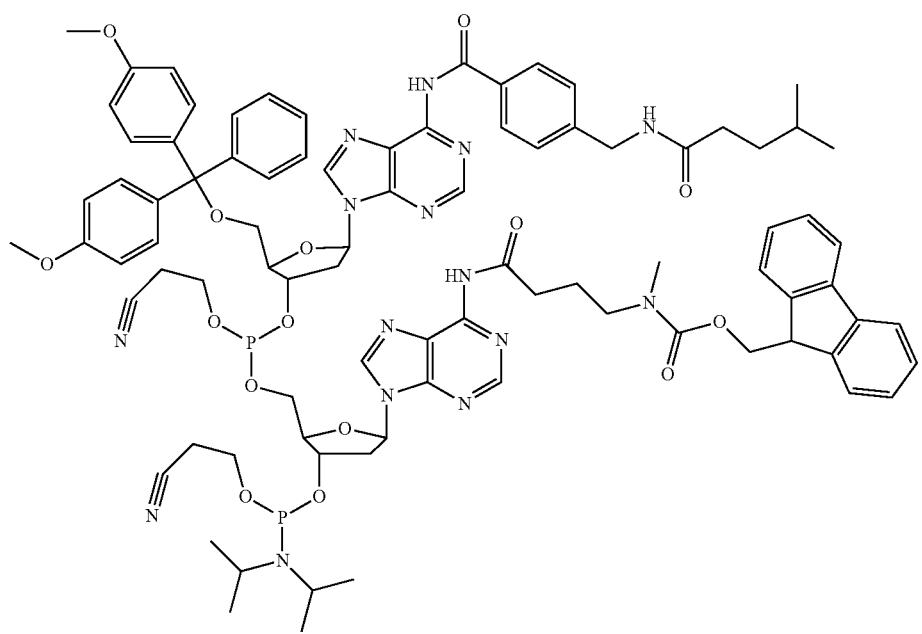

-continued
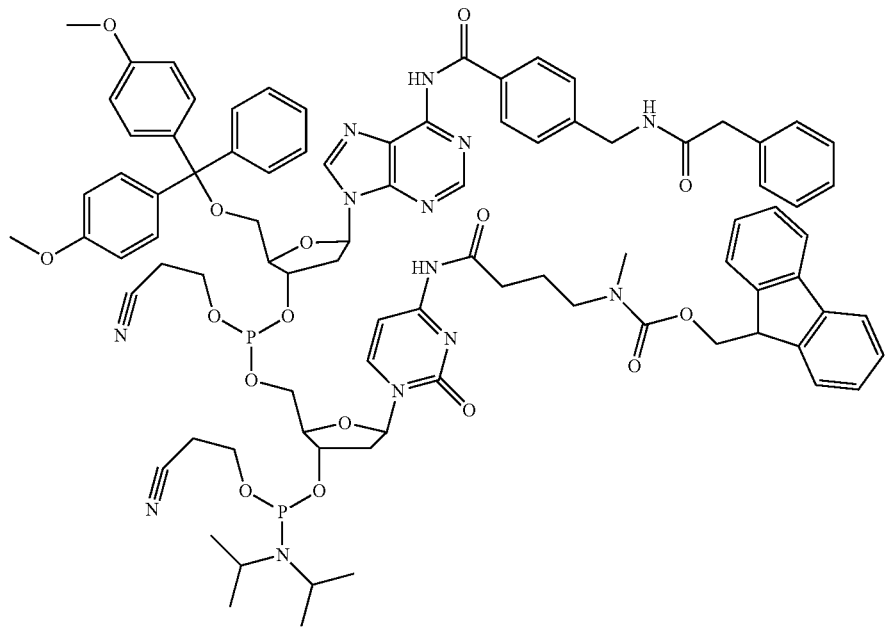
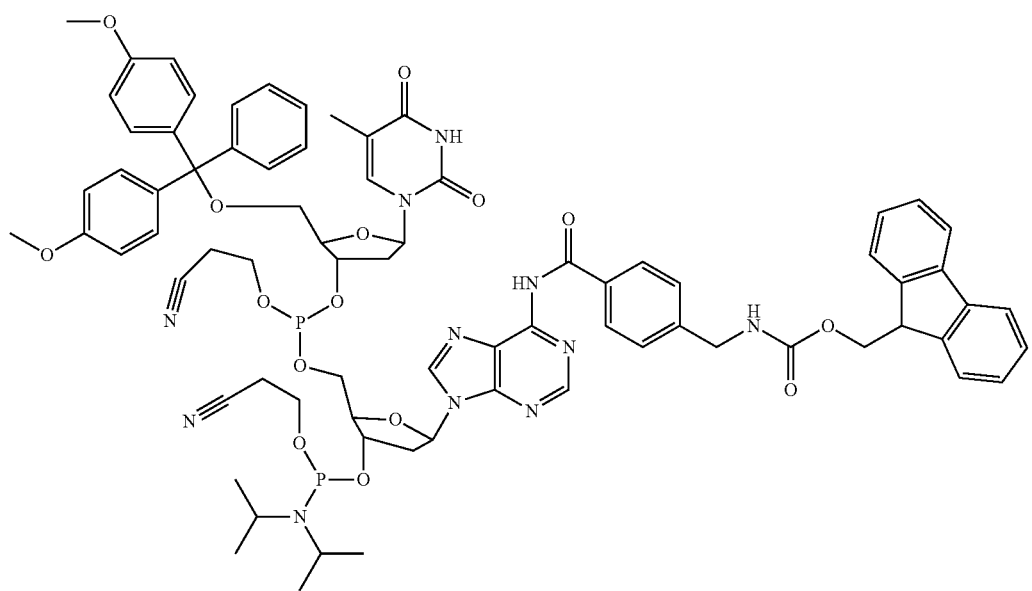

-continued
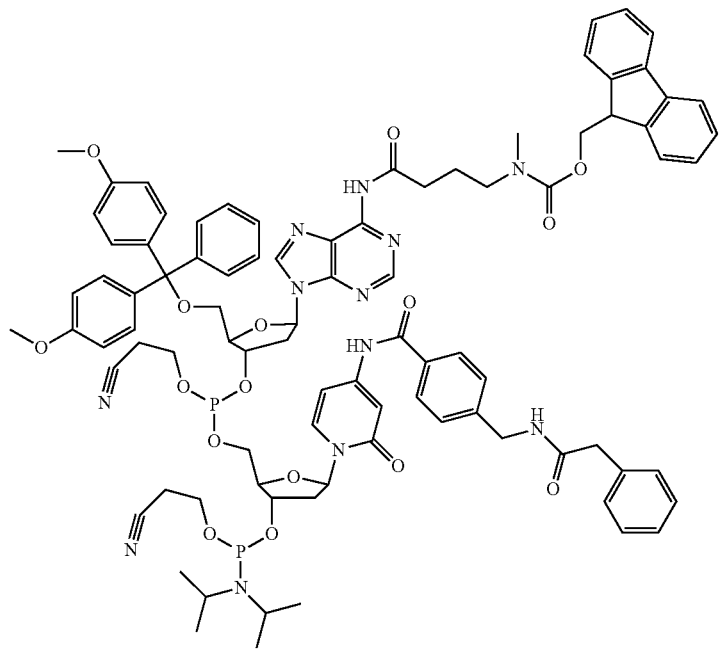
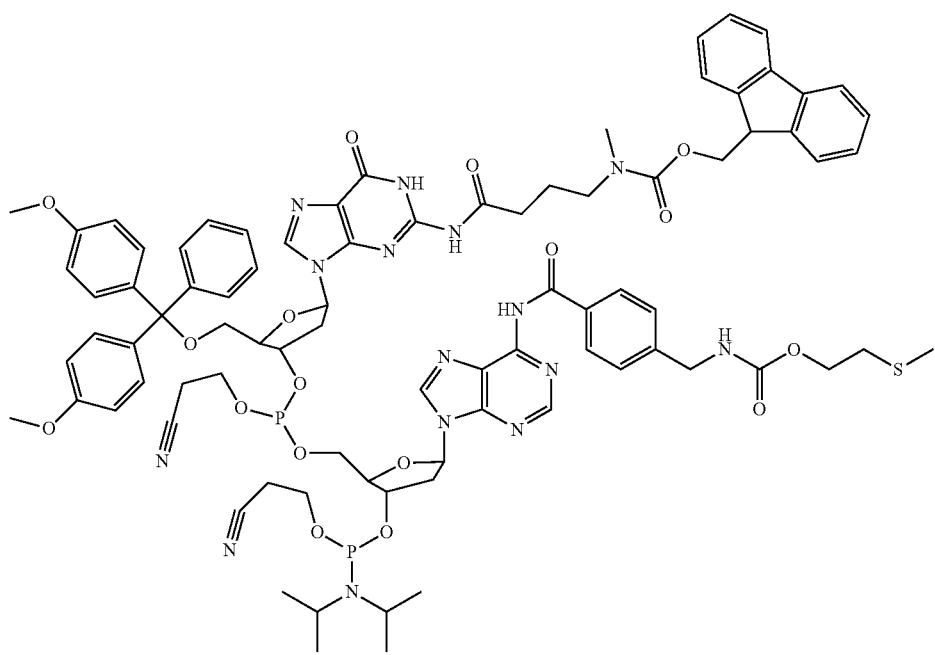

-continued
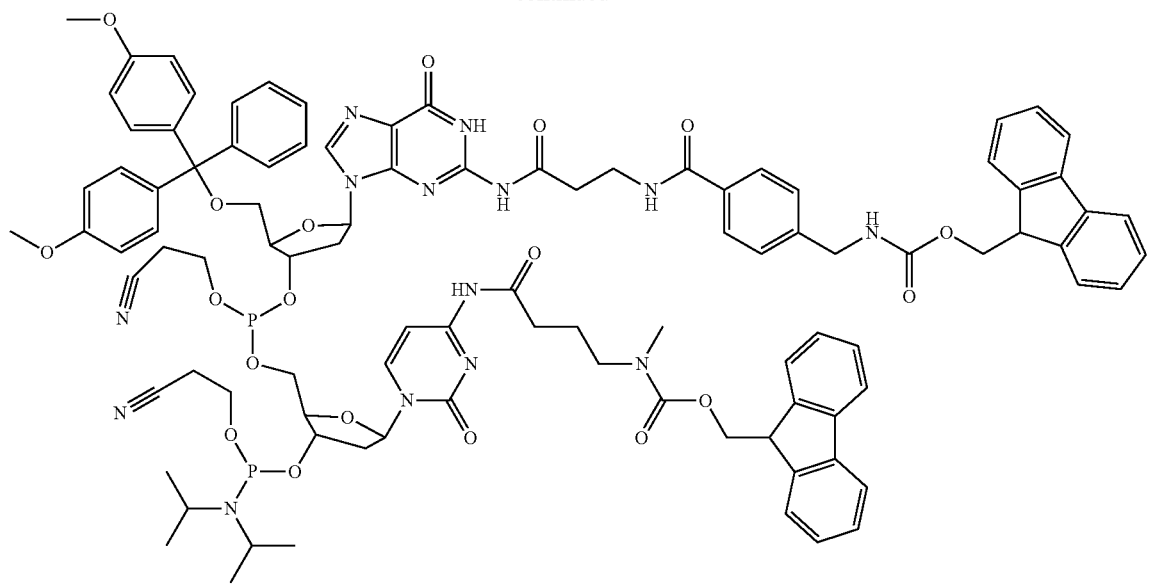
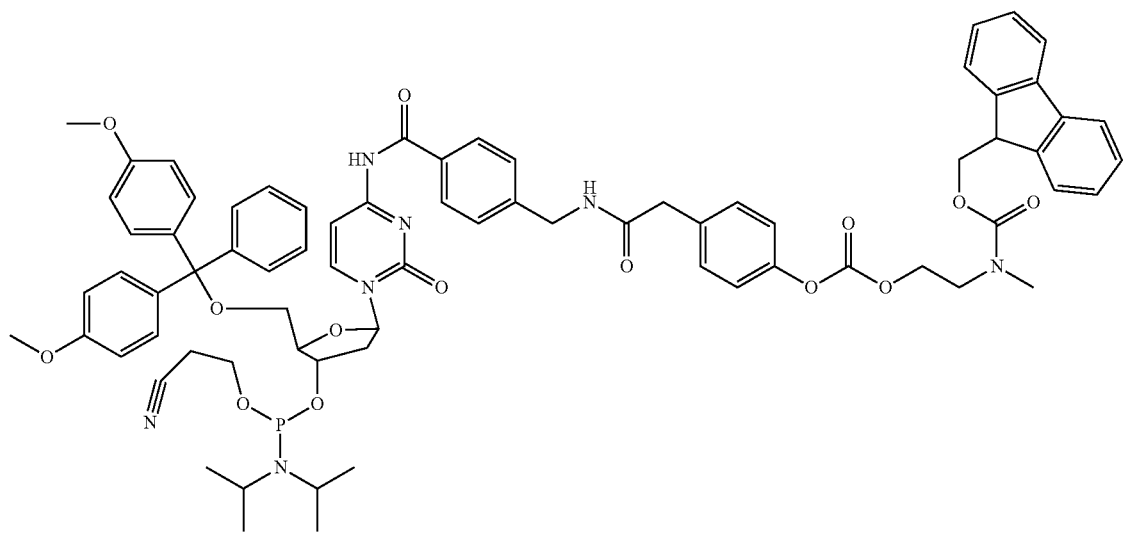
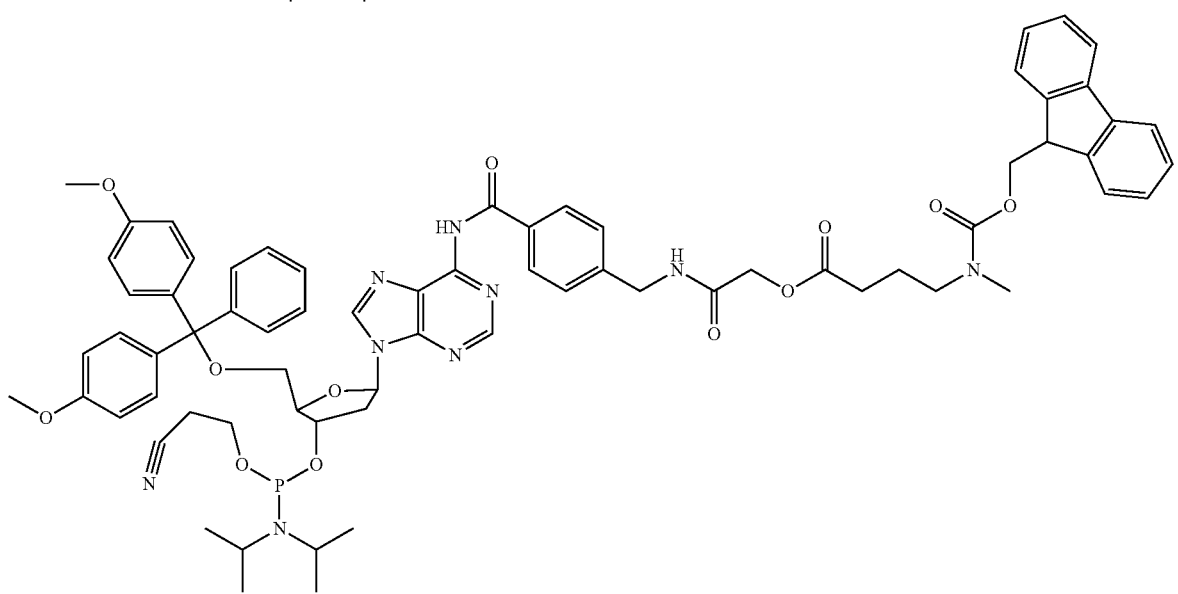

-continued
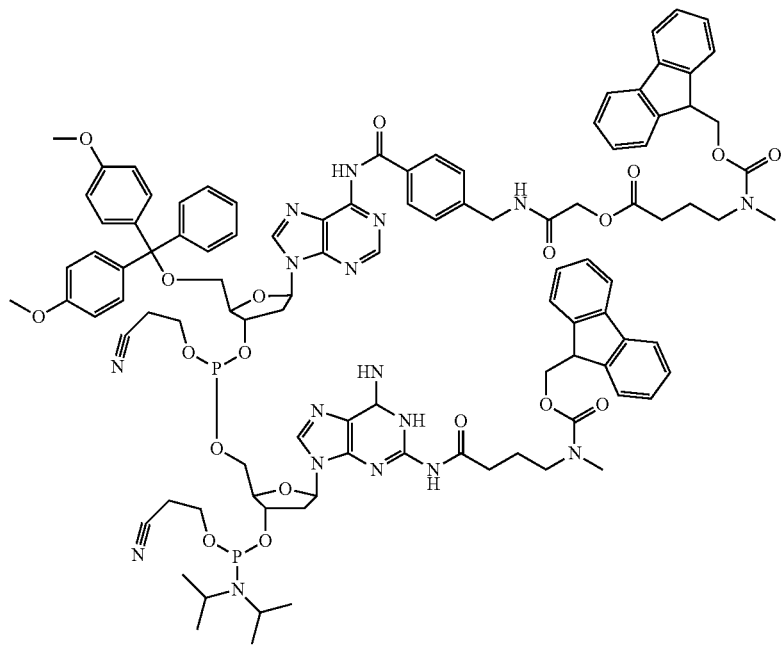
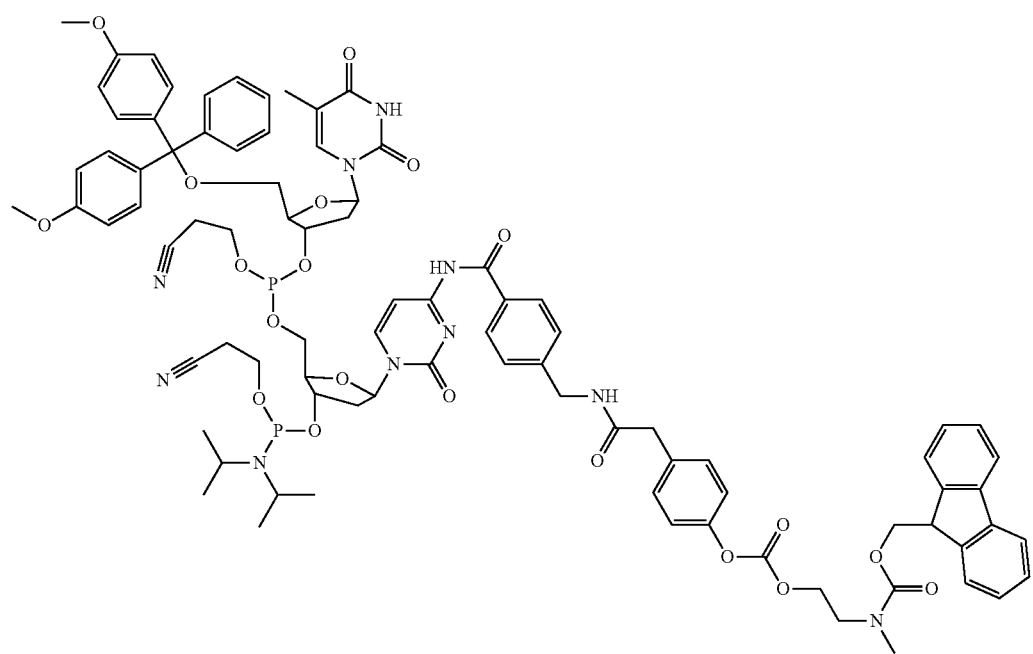

-continued

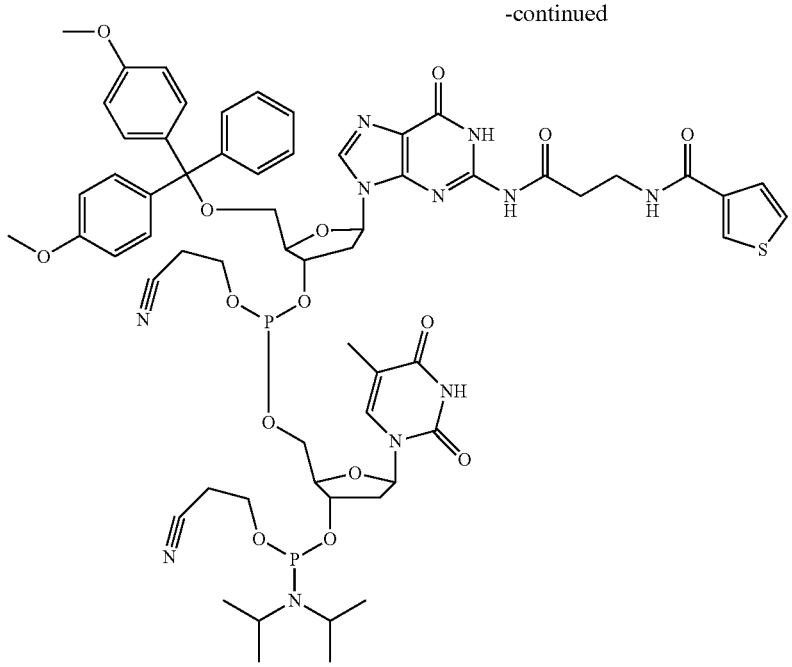

<<Substituent>> The substituent is not particularly limited and may be appropriately selected depending on the intended purpose. Examples of the substituent include a naturally occurring amino acid or non-naturally occurring amino acid, a metal complex, a fluorescent dye, an oxidation-reduction dye, a spin-labeling body, a hydrogen atom, an alkyl group having 1 to 10 carbon atoms and a group having any of the following formulas (101) to (110).

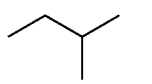
(101)

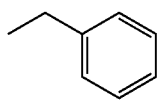
(102)

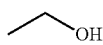
(103)

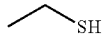
(104)

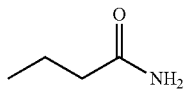
(105)

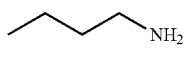
(106)

(107)

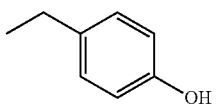
(108)

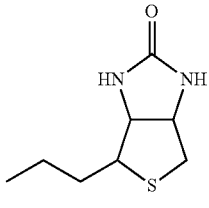
(109)

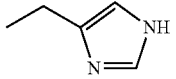
(110)

The naturally occurring or non-naturally occurring amino acid is not particularly limited and may be appropriately selected depending on the intended purpose. Examples thereof include valine, leucine, isoleucine, alanine, arginine, glutamine, lysine, asparagic acid, glutamic acid, proline, cysteine, threonine, methionine, histidine, phenylalanine, tyrosine, tryptophan, asparagine, glycine and serine.

The metal complex is not particularly limited, so long as it is a compound in which ligands are coordinated to a metal ion, and may be appropriately selected depending on the intended purpose. Examples thereof include Ru bipyridyl complexes, ferrocene complexes and nickel imidazole complexes.

The fluorescent dye is not particularly limited and may be appropriately selected depending on the intended purpose. Examples thereof include fluoroscein dyes, rhodamine dyes, eosin dyes and NBD dyes.

The oxidation-reduction dye is not particularly limited and may be appropriately selected depending on the intended purpose. Examples thereof include leuco dyes such as leucoaniline and leucoanthocyanin.

The spin labeling body is not particularly limited and may be appropriately selected depending on the intended purpose. Examples thereof include iron N-(dithiocarboxy)sarcosine and tetramethylpiperidine (TEMPO) derivatives.

The alkyl groups having 1 to 10 carbon atoms are not particularly limited and may be appropriately selected depending on the intended purpose. Examples thereof include methyl, ethyl, propyl, isopropyl, butyl, isobutyl, tert-butyl, pentyl, neopentyl, hexyl, cyclohexyl, octyl, nonyl and decyl.

Any of the above listed substituents may be further substituted.

—Protecting group for nucleic acid base— The protecting group for the nucleic acid base represented by Z' in General Formulas (III) and (IV) is not particularly limited and may be appropriately selected depending on the intended purpose. The protecting group is preferably a protecting group which is capable of being removed in an aprotic solvent; i.e., which is capable of being removed under mild conditions.

The protecting group for the nucleic acid base may be, for example, those described in JP-A Nos. 2007-225507, 2008-162992, 2008-230985 and 2009-062307. Also, the above indole group-protecting group may be used as the protecting group for the nucleic acid base.

—Protecting group for phosphoric acid group—In the nucleic acid-synthesizing amidite, in order to prevent unnecessary reactions during the synthesis of nucleic acids, a protecting group is preferably introduced to a reactive group of the phosphoric acid moiety which is not made to participate in condensation reaction during the synthesis of nucleic acids (in this specification, the protecting group may be referred to simply as a "protecting group for a phosphoric acid group"). The protecting group for a phosphoric acid group is preferably a protecting group which is capable of being removed in an aprotic solvent; i.e., which is capable of being removed under mild conditions. Here, the "protecting group which is capable of being removed under mild conditions" is similar to the above-described protecting group for the nucleic acid base. After the phosphite triester bond of the nucleic acid-synthesizing amidite has been oxidized to be a phosphate triester bond during the synthesis of nucleic acids, the protecting group on the phosphoric acid group in the phosphate triester bond is preferably removed under the above-described mild conditions.

Notably, in each of the nucleic acid-synthesizing amidites represented by General Formulas (II), (III) and (IV), a cyanoethyl group is exemplarily used as the protecting group for the phosphoric acid group. But, the protecting group for the phosphoric acid group is not limited thereto and may be appropriately selected depending on the purpose. Preferably, this protecting group is selected from the group consisting of a cyanoethyl group and derivatives thereof; a fluorenylmethyl group and derivatives thereof; a p-nitrophenethyl group and derivatives thereof; and a nitroethyl group and derivatives thereof.

SPECIFIC EXAMPLES

Specific examples of the nucleic acid-synthesizing amidite include those having the following Structural Formulas (1) and (2). The nucleic acid-synthesizing amidite should not be construed as being limited thereto.

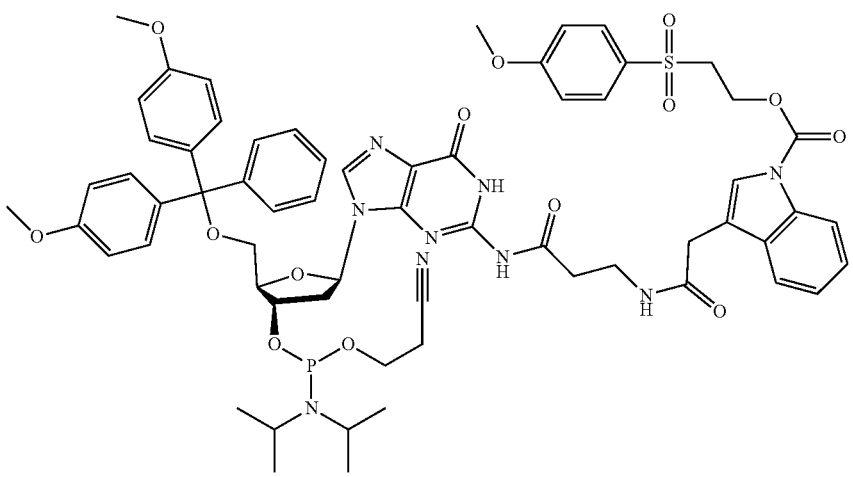

Structural Formula (1)

Structural Formula (2)

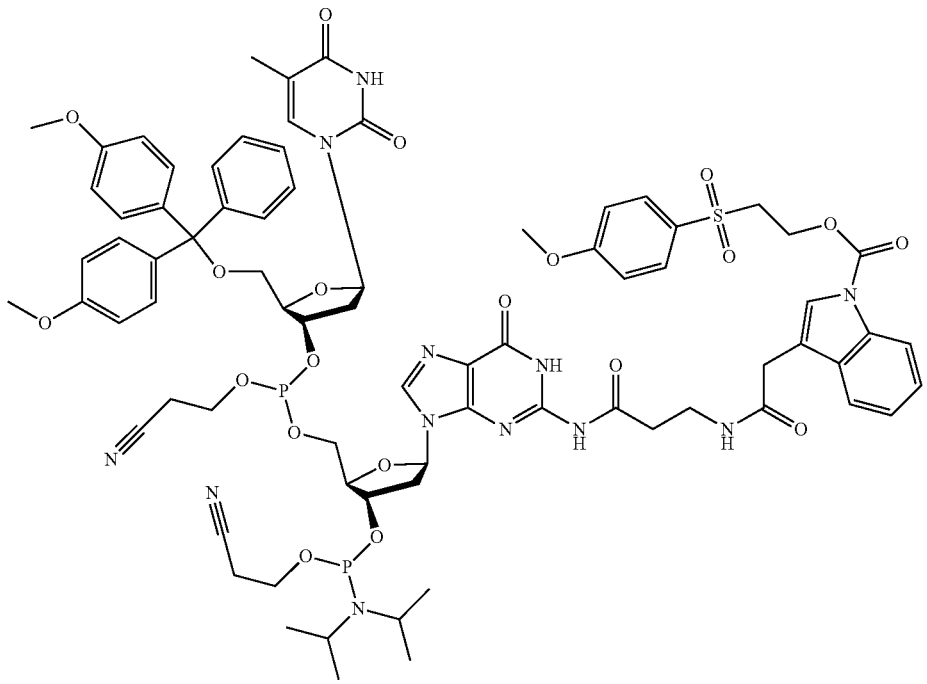

<Production> The method for synthesizing a monomer of the nucleic acid-synthesizing amidite having General Formula (II) or (III) is not particularly limited. The nucleic acid-synthesizing amidite may be synthesized by, for example, a method described below in Examples.

The method for synthesizing a dimer of the nucleic acid-synthesizing amidite having General Formula (II), (III) or (IV) is not particularly limited and may be appropriately selected depending on the intended purpose. For example, two monomers of the nucleic acid-synthesizing amidite may be linked together, or the monomer of the nucleic acid-synthesizing amidite may be linked with the above nucleoside compound.

The linking method for forming the dimer of the nucleic acid-synthesizing amidite is not particularly limited and may be appropriately selected depending on the intended purpose. Preferably, the dimer of the nucleic acid-synthesizing amidite preferably has a phosphite triester bond ($P(OR)_3$) as a linking moiety.

The dimer of the nucleic acid-synthesizing amidite represented by General Formula (II), (III) or (IV) has a phosphite triester bond as a linking moiety, and thus, is more stable under basic conditions than a dimer amidite having a phosphate triester bond as a linking moiety, allowing easy purification. Therefore, as compared with the dimer amidite having a phosphate triester bond as a linking moiety and being difficult to purify, the nucleic acid-synthesizing amidite can be obtained in high purity.

The compounds used in the reaction for forming the phosphite triester bond are not particularly limited and may be appropriately selected depending on the intended purpose. For example, phosphorous acid chloride and phosphorous acid dichloride may be used. From the viewpoint of suppressing side reactions, a method described in the below-given Examples is thought to be preferred.

The nucleic acid-synthesizing amidite can be deprotected under mild conditions, and thus, the protecting group can be readily removed without removal of the indole group.

(Precursor of nucleic acid-synthesizing amidite) The precursor of a nucleic acid-synthesizing amidite is that of the above nucleic acid-synthesizing amidite and has any of the following Structural Formulas (3) to (7):

Structure Formula (3)

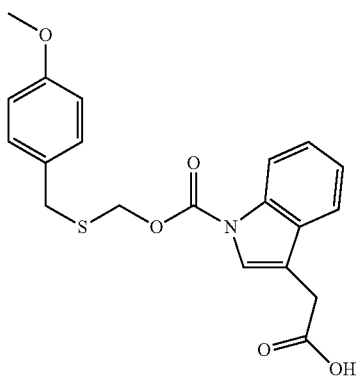

Structure Formula (4)

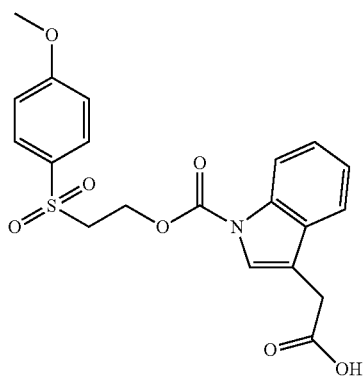

Structure Formula (5)

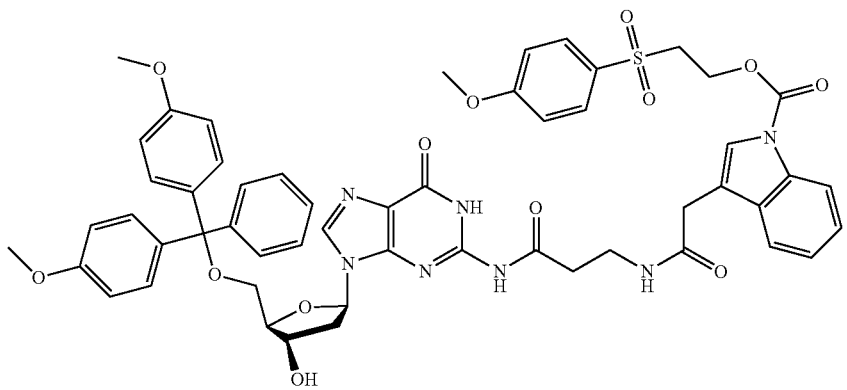

Structure Formula (6)

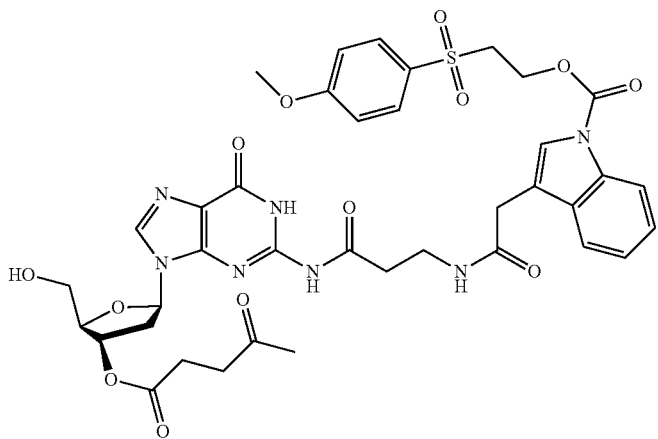

Structure Formula (7)

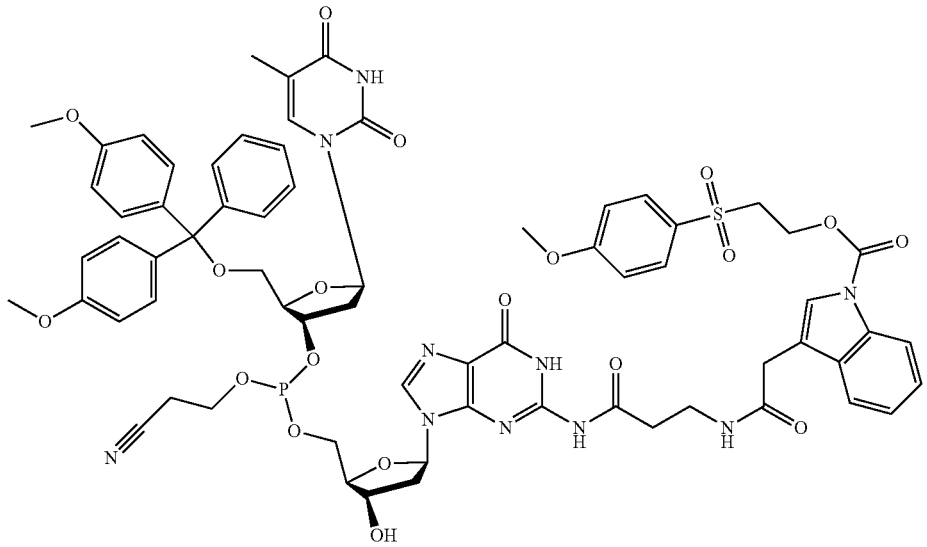

The precursor of the nucleic acid-synthesizing amidite exists stably in the synthesis pathway of the nucleic acid-synthesizing amidite. Thus, the nucleic acid-synthesizing amidite can be obtained in high yield via the precursor of the nucleic acid-synthesizing amidite.

(Nucleic acid-synthesizing method) The nucleic acid-synthesizing method uses the nucleic acid-synthesizing amidite.

The nucleic acid-synthesizing method is not particularly limited, as long as nucleic acids can be synthesized using the nucleic acid-synthesizing amidite, and may be appropriately selected depending on the intended purpose. Examples thereof include conventional nucleic acid-synthesizing methods in which a solid-phase method is combined with the condensation reaction by a diester method, a triester method, a phosphite method, a phosphoramidite method, an H-phosphonate method and a thiophosphite method.

Also, the nucleic acid-synthesizing method can be conducted using a conventional automated nucleic acid synthesizer, for example.

In the nucleic acid-synthesizing method, one type of the nucleic acid-synthesizing amidite may be used, or two types of the nucleic acid-synthesizing amidite may be used in combination. Also, as the amidite used in the nucleic acid-synthesizing method, the above nucleic acid-synthesizing amidites may be used alone or in combination with other amidites.

In the latter case, the other amidites are preferably those which can be deprotected under the above-described mild conditions. Such amidites may be, for example, those described in JP-A Nos. 2008-162992, 2008-230985 and 2009-062307.

In the above nucleic acid-synthesizing method, condensation reaction is performed between the nucleic acid-synthesizing amidite and the nucleic acid-synthesizing amidite or the other amidites, and then the protecting group is removed from the nucleic acid-synthesizing amidite or the other amidites.

The condensation reaction is not particularly limited and may be appropriately selected from known methods depending on the intended purpose. Examples thereof include solid phase reaction and liquid phase reaction.

The solid phase reaction can be performed, for example, as follows. Specifically, the condensation reaction between (deoxy)ribonucleoside present on a solid phase resin and an acetonitrile solution of 0.03M to 0.1M amidite which is 1.5 equivalents to 10 equivalents relative to the hydroxyl group of the sugar of the (deoxy)ribonucleoside is performed in an acetonitrile solution of 0.1M to 0.5M tetrazole or tetrazole derivative at a temperature of 50° C. or lower within 30 minutes.

The liquid phase reaction can be performed, for example, as follows. Specifically, the condensation reaction between (deoxy)ribonucleoside and amidite which is 0.85 equivalents to 1.2 equivalents relative to the hydroxyl group of the sugar of the (deoxy)ribonucleoside is performed in an acetonitrile solution containing tetrazole or a tetrazole derivative which is 1 equivalent to 5 equivalents relative to the hydroxyl group of the sugar of the (deoxy)ribonucleoside at a temperature of 50° C. or lower within 6 hours.

The tetrazole derivative is not particularly limited and may be appropriately selected depending on the intended purpose. Examples thereof include 5-benzylthio-1H-tetrazole (BTT), 5-ethylthio-1H-tetrazole (ETT) and 5-[3,5-bis(trifluoromethyl)phenyl]-1H-tetrazole. These may be used alone or in combination.

The conditions for the deprotection (removal of the protecting group) are not particularly limited and may be appropriately selected depending on the intended purpose. The protecting group is preferably removed under the above-described mild conditions. For example, it is preferred that the protecting group be removed by a bulky base in an aprotic solvent.

The aprotic solvent and the bulky base are the same as those described above. Also, the concentration and the time required for the deprotection are the same as those described above.

The above nucleic acid-synthesizing method uses the above nucleic acid-synthesizing amidite, and thus, the protecting group is capable of being removed under mild conditions under which the indole group thereof is not removed. Thus, the nucleic acid-synthesizing method can produce nucleic acids consistently.

(Nucleic acid) The nucleic acid is obtained by the above nucleic acid-synthesizing method. That is, the nucleic acid contains, as at least a part thereof, a modified nucleotide unit having an indole group.

The number of nucleotide units constituting the nucleic acid is not particularly limited and may be appropriately selected depending on the intended purpose. For example, it is preferably 10 to 200, more preferably 20 to 100, particularly preferably 30 to 80.

Notably, among the nucleotide units constituting the nucleic acid, the rate of the modified nucleotide units derived from the nucleic acid-synthesizing amidites is not particularly limited and may be appropriately selected depending on the intended purpose.

The nucleic acid may be a DNA or RNA sequence, and the DNA or RNA sequence may be a single- or double-strand.

The above nucleic acid has an indole group, and can bind to target substances (e.g., proteins) via the indole group. Thus, the nucleic acid can be suitably used for analyses of these target substances.

EXAMPLES

Hereinafter, the examples of the present invention will be specifically explained, but these examples shall not be construed as to limit the scope of the present invention. Note that "%" in the following Examples and Test Examples is "mol %" unless otherwise specified.

Example 1

Synthesis of Nucleic Acid-Synthesizing Amidite

A nucleic acid-synthesizing amidite having Structural Formula (1) and a nucleic acid-synthesizing amidite having Structural Formula (2) were synthesized as follows.

A protecting group used was a group represented by General Formula (I) where R is a p-methoxyphenyl group.

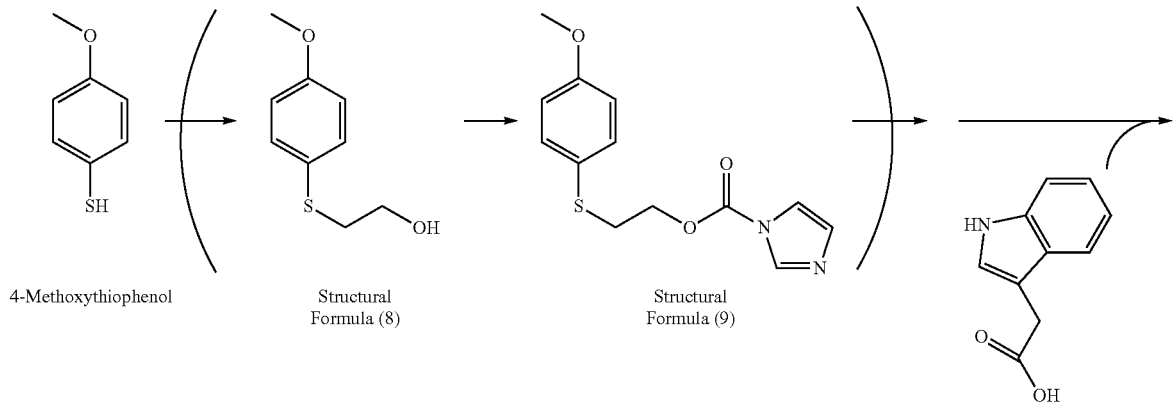

4-Methoxythiophenol   Structural Formula (8)   Structural Formula (9)

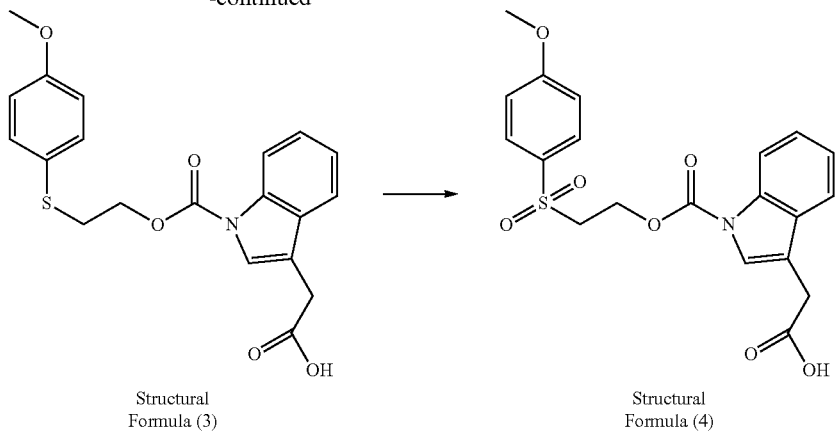

Structural Formula (3)   Structural Formula (4)

<Synthesis of compound having Structural Formula (3)>
Chloroethanol (5.0 mL, 74.9 mmol) was dissolved in dehydrated dimethylformamide (100 mL), and 4-methoxythiophenol (8.7 mL, 71.3 mmol) was added to the resultant solution. Then, the reaction mixture was purged with nitrogen gas for 5 minutes. Subsequently, sodium carbonate (31 g, 224 mmol) was added thereto, and the resultant mixture was left to stand still under ice cooling for 15 minutes, followed by agitating at room temperature for 30 minutes. The reaction mixture was diluted with ethyl acetate and then washed with water. The ethyl acetate solution was concentrated under reduced pressure, to thereby obtain 13.04 g of a compound having Structural Formula (8).

Triphosgene (7.00 g, 23.59 mmol) was dissolved in dehydrated tetrahydrofuran (80 mL), followed by cooling with ice. Subsequently, a mixed solution of the compound having Structural Formula (8) (13.04 g, up to 70.78 mmol), pyridine (6.01 mL, 74.32 mmol) and dehydrated tetrahydrofuran (80 mL) was added dropwise to the cooled solution for about 30 minutes. The resultant mixture was agitated at room temperature for 30 minutes and cooled with ice. Then, imidazole (4.82 g, 70.78 mmol) and pyridine (6.01 mL, 74.32 mmol) were added to the cooled mixture, and the resultant mixture was agitated at room temperature for 30 minutes. Thereafter, hexane (160 mL) was added to the reaction mixture, followed by agitating and filtrating. The filtrated product was washed with a solvent mixture of tetrahydrofuran and hexane (1:1 (by volume)). The filtrate and washing liquid were concentrated under reduced pressure, to thereby obtain 20.02 g of a compound having Structural Formula (9).

3-Indoleacetic acid (11.27 g, 64.35 mmol) was dissolved in dehydrated dimethylformamide (130 mL). Subsequently, a 60% by mass sodium hydride-oil mixture (5.66 g, 141.6 mmol) was added to the resultant solution, followed by agitating at room temperature for 1 hour and cooling with ice. Thereafter, a cold solution of the compound having Structural Formula (9) (20.02 g, up to 70.78 mmol) in dehydrated dimethylformamide (71 mL) was added to the cooled mixture. Subsequently, the resultant mixture was agitated for 5 minutes and then at room temperature for 30 minutes. Thereafter, ammonium chloride (13.8 g) was added to the reaction mixture, and the resultant mixture was concentrated under reduced pressure. The residue was dissolved in ethyl acetate, followed by washing with water. The ethyl acetate solution was concentrated under reduced pressure, and the residue was purified by medium pressure chromatography (1% acetic acid (constant), ethyl acetate:hexane=1:2→1:1 (by volume)), to thereby obtain 12.52 g (32.48 mmol) of a compound having Structural Formula (3).

<Synthesis of compound having Structural Formula (4)>
The compound having Structural Formula (3) (10.11 g, 26.23 mmol) was dissolved in dichloromethane (66 mL). Under cooling with ice, 13.28 g of 70% m-chloroperoxybenzoic acid in water was added to the resultant solution, followed by agitating for 30 minutes. The reaction solution was washed with water, and the dichloromethane solution was concentrated under reduced pressure. The residue was purified by medium pressure chromatography (2% acetic acid (constant), dichloromethane:ethyl acetate=1:0→4:1 (by volume)), to thereby obtain 8.91 g (21.34 mmol, 81%) of a compound having Structural Formula (4).

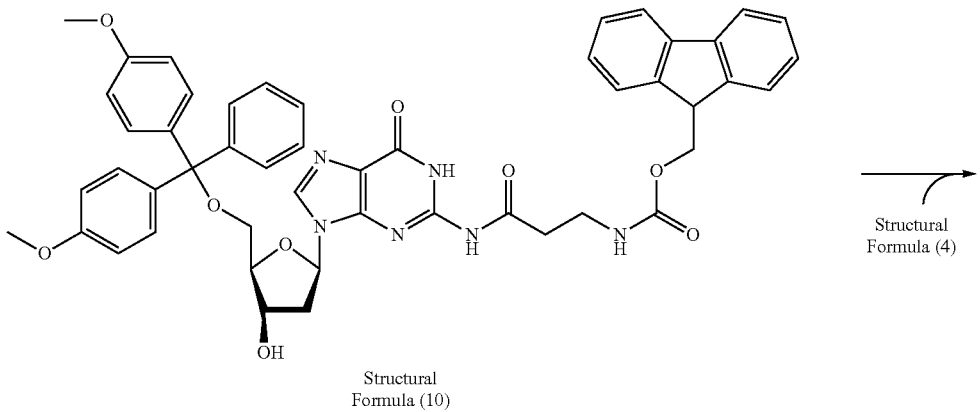

Structural Formula (10)

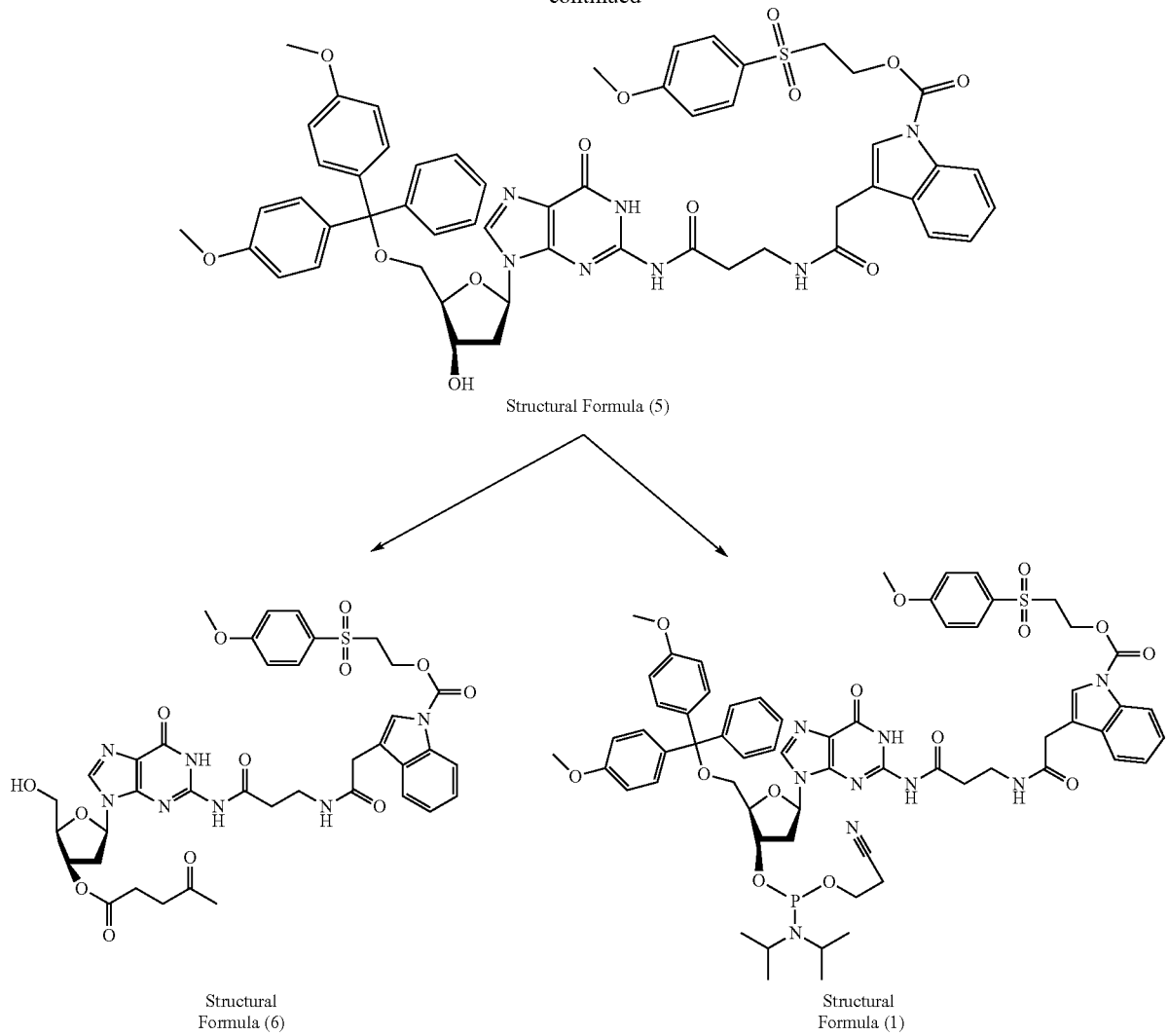

Structural Formula (5)

Structural Formula (6)

Structural Formula (1)

<Synthesis of compound having Structural Formula (10)>
A compound having Structural Formula (10) was synthesized by the synthesis method for Compound XIV described in JP-A No. 2008-230985.

<Synthesis of compound having Structural Formula (5)>
The compound having Structural Formula (10) (18.42 g, 21.34 mmol) was dissolved in dehydrated dichloromethane (42 mL). Subsequently, triethylsilane (5.11 mL, 32.01 mmol) and diazabicycloundecene (4.79 mL, 32.01 mmol) were added to the resultant solution, followed by agitating at room temperature for 10 minutes. Thereafter, triethylamine hydrochloride (5.29 g, 38.41 mmol) was added to the mixture, followed by agitating for 5 minutes or longer, to thereby obtain solution A.

The compound having Structural Formula (4) (8.91 g, 21.34 mmol) was dissolved in dehydrated dimethoxyethane, and the resultant solution was concentrated under reduced pressure three times. The residue was suspended in dehydrated dichloromethane (65 mL). Subsequently, diisopropylethylamine (4.09 mL, 23.47 mmol) and O-benzotriazolyl-N,N,N',N'-tetramethyluronium hexafluorophosphate (8.50 g, 22.41 mmol) were added to the suspension, followed by agitating at room temperature for 30 minutes. The resultant solution was added to the above-prepared solution A, and the mixture was agitated at room temperature for 30 minutes. The reaction solution was washed with water, and the dichloromethane solution was concentrated under reduced pressure. The residue was purified by medium pressure chromatography (ethyl acetate:ethanol=19:1→9:1 (by volume)), to thereby obtain 21.30 g (20.48 mmol, 96%) of a compound having Structural Formula (5).

<Synthesis of nucleic acid-synthesizing amidite having Structural Formula (1)> The compound having Structural Formula (5) (15.88 g, 15.27 mmol) was dissolved in a solvent mixture of dehydrated acetonitrile and dehydrated dichloromethane, and the resultant solution was concentrated under reduced pressure three times. The residue was dissolved in dehydrated dichloromethane (46 mL). Under cooling with ice, dimethylaminopyridine (93 mg, 0.76 mmol) and diisopropylethylamine (3.02 mL, 18.32 mmol) were added to the resultant solution, and then a solution of 2-cyanoethyldiisopropylchlorophosphoroamidite (3.75 mL, 16.80 mmol) in methylene chloride (15 mL) was added dropwise to the mixture for 5 minutes or longer. The thus-obtained mixed solution was agitated under cooling with ice for 5 minutes and left to stand still at 4° C. overnight. Then, methanol (3.0 mL) was added to the mixture, followed by agitating for 30 minutes. The reaction solution was washed with water, and the dichloromethane solution was concentrated under reduced pressure. The residue was purified by medium pressure chromatography (2% pyridine-containing ethyl acetate-hexane (2:1 (by volume)): 2% pyridine and 7% ethanol-containing ethyl acetate=1:0→0:1 (by volume)), to thereby obtain 14.96 g (79%) of a nucleic acid-synthesizing amidite having Structural Formula (1).

<Synthesis of compound having Structural Formula (6)>
The compound having Structural Formula (5) (21.30 g, 20.48 mmol) was dissolved in dehydrated dioxane, and the resultant solution was concentrated under reduced pressure three times. The residue was dissolved in dehydrated dioxane (62 mL). Subsequently, dimethylaminopyridine (150 mg, 1.2 mmol), dicyclohexylcarbodiimide (6.34 g, 30.72 mmol) and levulinic acid (3.15 mL, 30.72 mmol) were added to the resultant solution, followed by agitating at room temperature for 1 hour. Thereafter, methanol (4 mL) was added to the reaction solution, followed by agitating for 30 minutes. The insoluble matter was removed through filtration, and the filtrate was concentrated under reduced pressure, diluted with dichloromethane, and washed with water. The dichloromethane solution was concentrated under reduced pressure, and the residue was dissolved in dehydrated dichloromethane (97 mL). Under cooling with ice, trifluoloacetic acid (7.2 mL) was added to the resultant solution, and the mixture was agitated at 0° C. for 1 hour. Subsequently, dehydrated methanol (82 mL) and dehydrated pyridine (11 mL) were added thereto. The reaction mixture was agitated at room temperature overnight. The reaction mixture was washed with water, and the dichloromethane solution was concentrated under reduced pressure. The residue was purified by medium pressure chromatography (dichloromethane:ethanol=19:1→91:9 (by volume)), to thereby obtain 14.69 g (86%) of a compound having Structural Formula (6).

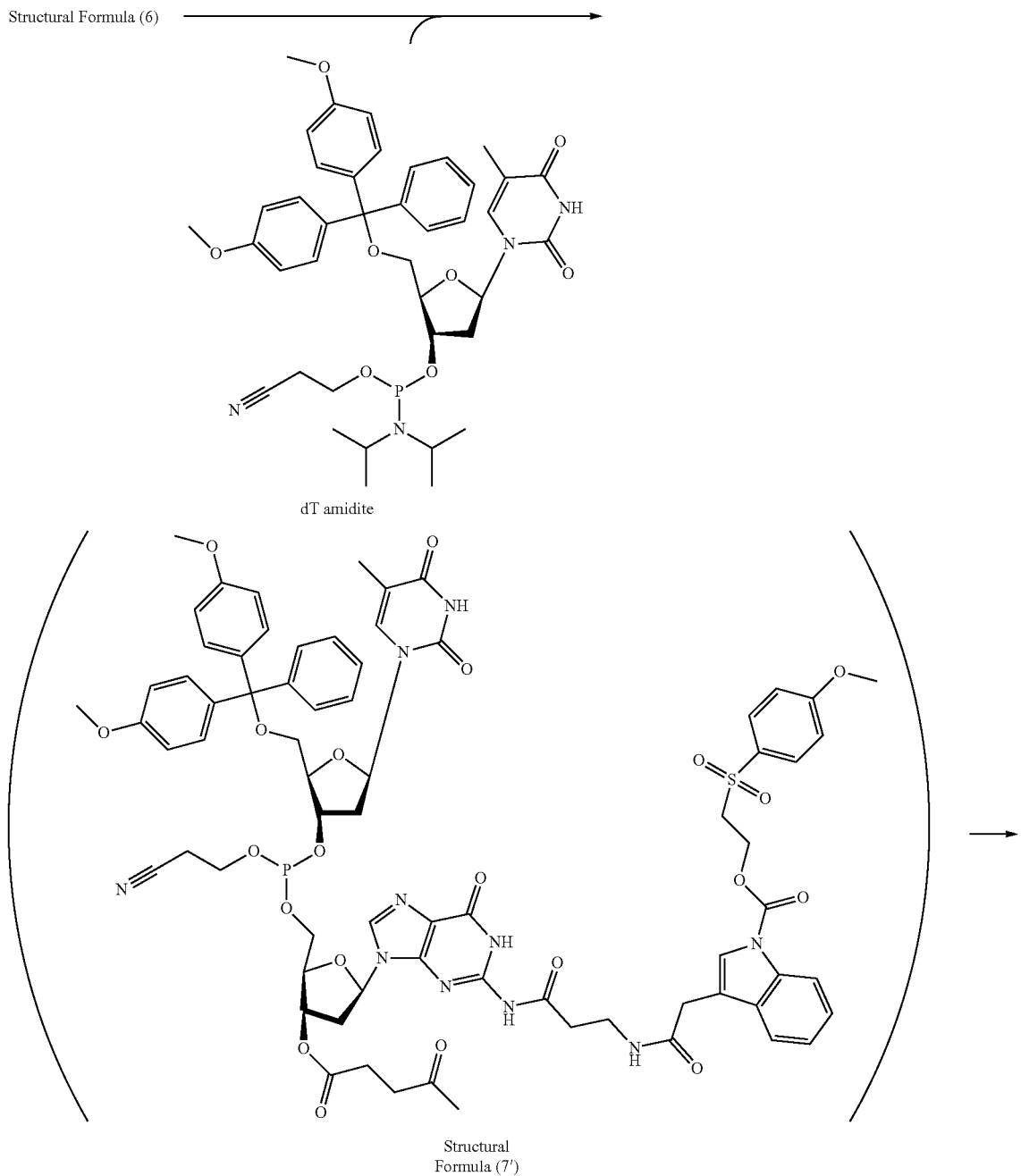

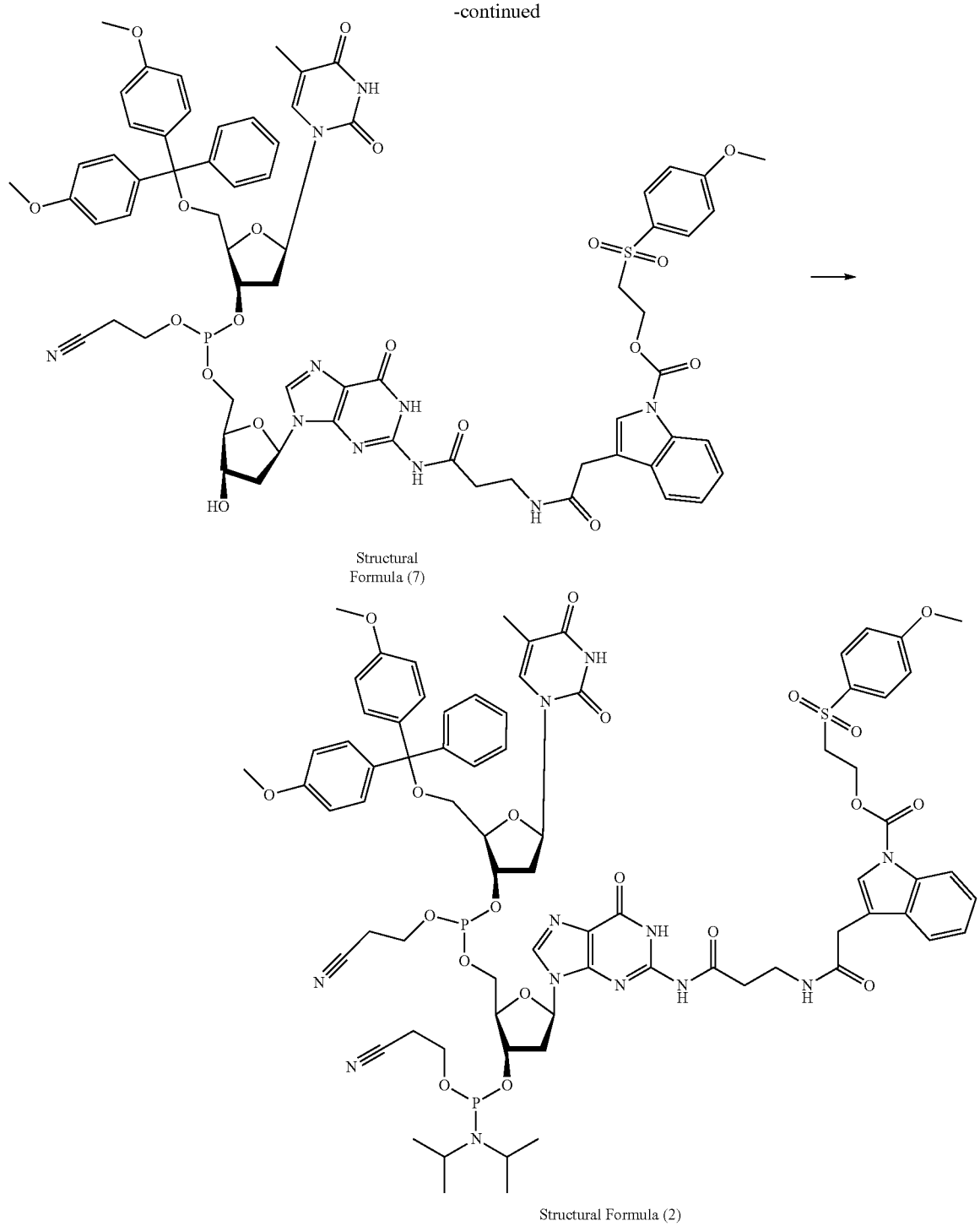

Structural Formula (7)

Structural Formula (2)

<Synthesis of compound having Structural Formula (7)>
The compound having Structural Formula (6) (12.54 g, 15.0 mmol) and a dT amidite (product of Glen Research Corp.) (11.50 g, 15.44 mmol) were dissolved in dehydrated acetonitrile, and the resultant solution was concentrated under reduced pressure three times. The residue was dissolved in dehydrated acetonitrile (60 mL). Subsequently, tetrazole (5.25 g, 75.0 mmol) was added to the resultant solution, followed by agitating at room temperature for 30 minutes. Then, methanol (3.0 mL) was added to the mixture, followed by agitating for 30 minutes. The resultant solution was diluted with dichloromethane and then washed with water. The dichloromethane solution was concentrated under reduced pressure. The residue was dissolved in pyridine (75 mL). Under cooling with ice, a solution (22.5 mL) of 1M hydrazine monohydrate-containing pyridine and acetic acid (5:2 (by volume)) was added to the resultant solution, followed by agitating at 0° C. for 30 minutes. Until it was confirmed that a compound having Structural Formula (7') disappeared, the solution (7.5 mL) of 1M hydrazine monohydrate-containing pyridine and acetic acid (5:2 (by volume)) was added thereto every 15 minutes Under cooling with ice, acetone (37.5 mL) was added thereto, followed by agitating at 0° C. for 10 minutes. The resultant mixture was diluted with dichloromethane and then washed with water. The dichloromethane solution was concentrated under reduced pressure. The residue was purified by medium pressure chromatography (dichloromethane:ethanol=94:6→9:1 (by volume)), to thereby obtain 15.1 g (73%) of a compound having Structural Formula (7).

<Synthesis of nucleic acid-synthesizing amidite having Structural Formula (2)> The compound having Structural Formula (7) (15.10 g, 10.93 mmol) was dissolved in a solvent mixture of dehydrated acetonitrile and dichloromethane, and the resultant mixture was concentrated under reduced pressure three times. The residue was dissolved in dehydrated dichloromethane (40 mL). Under cooling with ice, dimethylaminopyridine (66 mg, 5.45 mmol) and diisopropylethylamine (2.28 mL, 13.11 mmol) were added to the resultant solution, and a diluted solution of 2-cyanoethyldiisopropylchlorophosphoroamidite (2.68 mL, 12.02 mmol) in dichloromethane (11 mL) was added thereto. The mixed solution was agitated at 4° C. overnight. Subsequently, methanol (2.2 mL) was added thereto, followed by agitating for 30 minutes. The reaction solution was diluted with dichloromethane and then washed with water. The dichloromethane solution was concentrated under reduced pressure. The residue was purified under the following conditions: 2% pyridine-containing dichloromethane-hexane (2:1 (by volume)): 2% pyridine-containing dichloromethane=0:100→100:0, and then, 2% pyridine-containing dichloromethane: 2% pyridine, 20% ethanol and 2% pyridine-containing dichloromethane=1:0→3:1 (by volume), to thereby 11.06 g (62%) of a nucleic acid-synthesizing amidite having Structural Formula (2).

<Structural analysis of compounds> Each of the above compounds (having Structural Formulas (1) to (7)) was synthesized for structure as follows. The results are shown in FIGS. 1 to 12.

—$^1$H-NMR— Each sample (about 5 mg) was dissolved in deuterated dimethyl sulfoxide (DMSO). The proton nuclear magnetic resonance spectrum was measured at 300.4 MHz and 18° C. to 20° C. The internal standard used was a peak of the residual undeuterated dimethyl sulfoxide.

—$^{31}$P-NMR— Each sample (about 5 mg) was dissolved in deuterated dimethyl sulfoxide. The $^{31}$P nuclear magnetic resonance spectrum was measured at 121.5 MHz and 20° C. The external standard used was a peak (−6.2 ppm) of triphenylphosphine (PPh$_3$). The measurement was performed at the BCM mode.

—HH cosy— Each sample (about 5 mg) was dissolved in deuterated dimethyl sulfoxide. The HH cosy spectrum was measured at 300.4 MHz and 20° C. The internal standard used was a peak of the deuterated dimethyl sulfoxide.

Example 2

Confirmation of Removal of Protecting Group in Nucleic Acid-Synthesizing Amidite Having Structural Formula (1)

As described below, it was confirmed that the nucleic acid-synthesizing amidite obtained in Example 1 (i.e., the nucleic acid-synthesizing amidite having Structural Formula (1)) was able to be deprotected under mild conditions.

Figure 8:
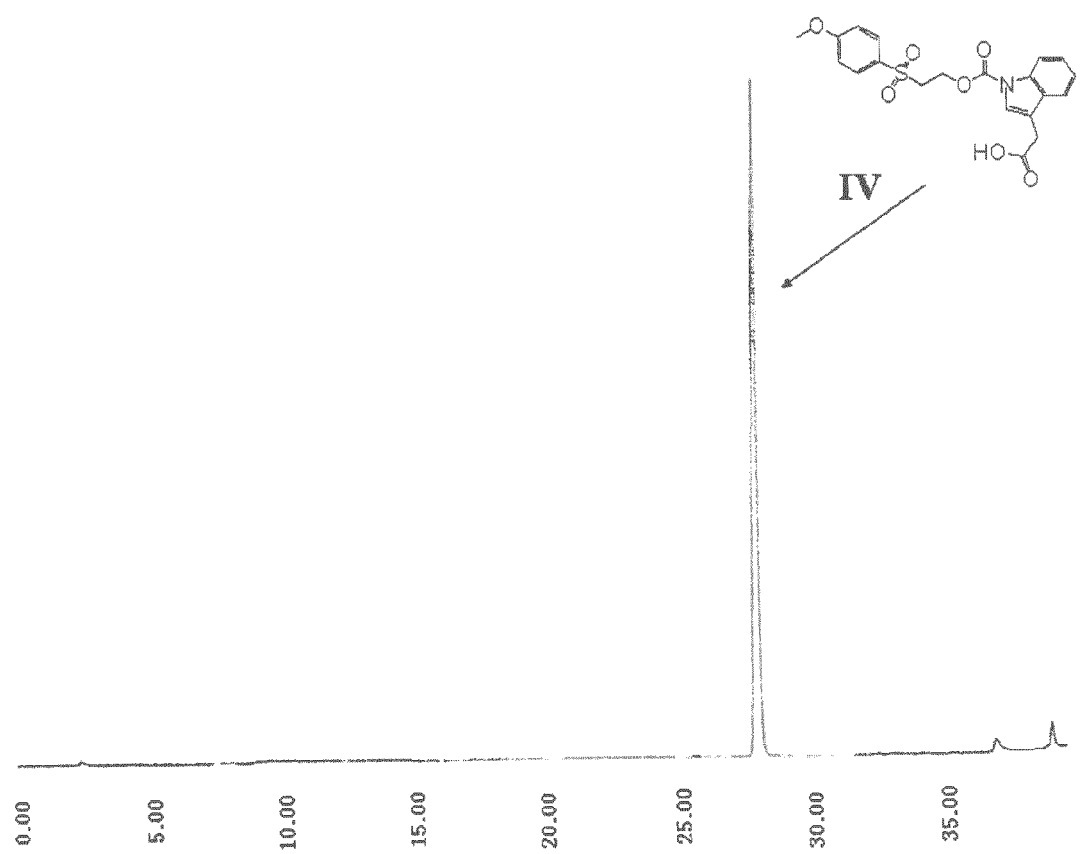
FIG. 8 is an HPLC chart 1 in Example 2.
Figure 9:
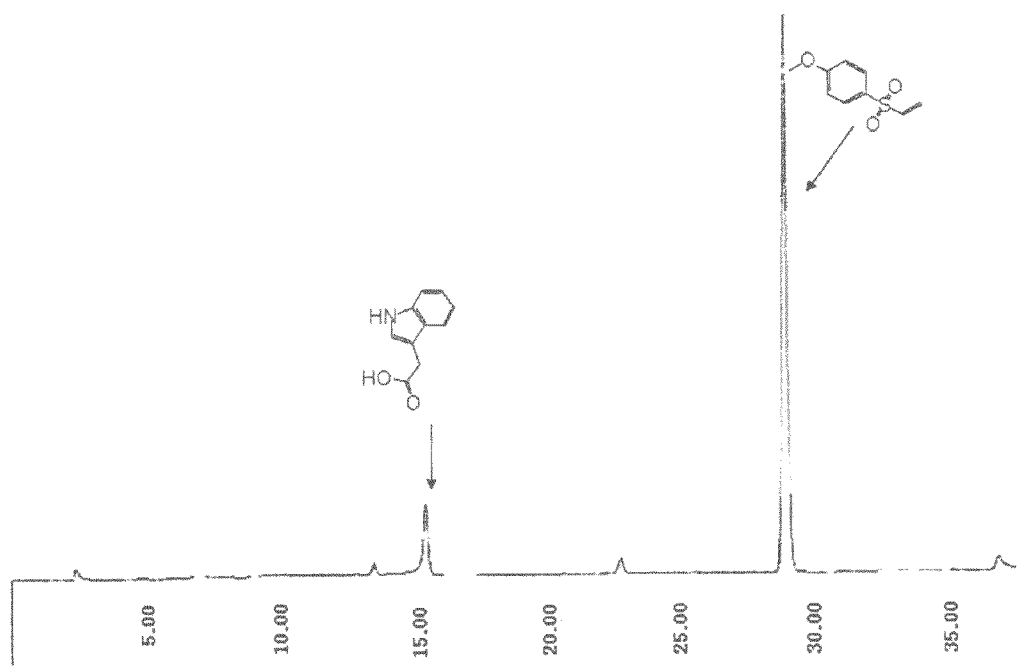
FIG. 9 is an HPLC chart 2 in Example 2.
Figure 10:
FIG. 10 is a HPLC chart 3 in Example 2.
Figure 11:
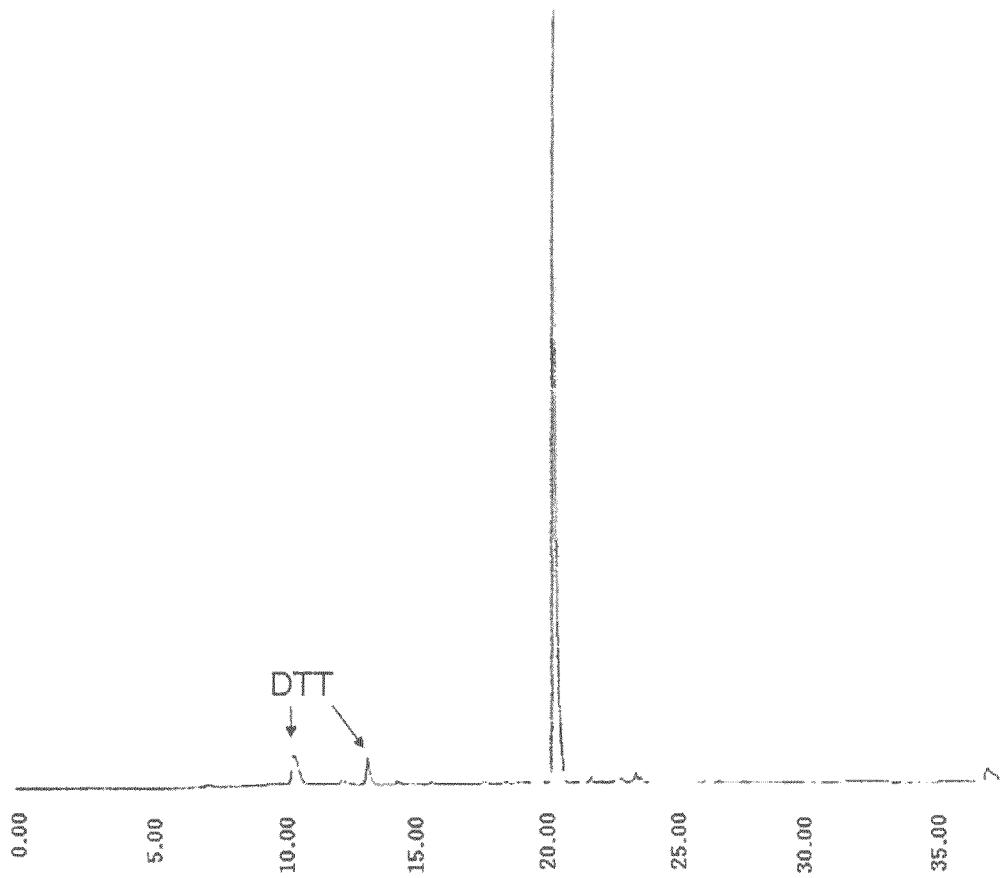
FIG. 11 is a HPLC chart 4 in Example 2.
Figure 12:
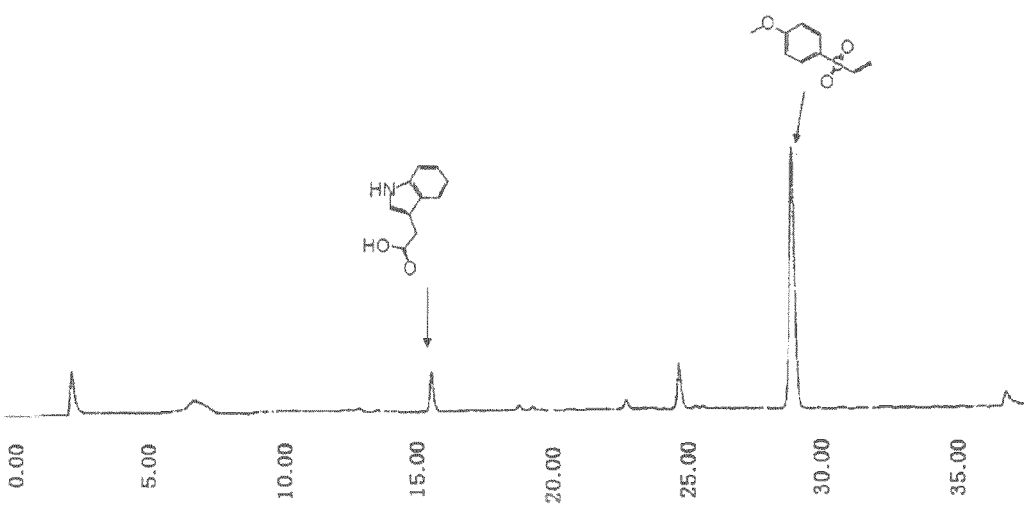
FIG. 12 is a HPLC chart 5 in Example 2.
Figure 13:
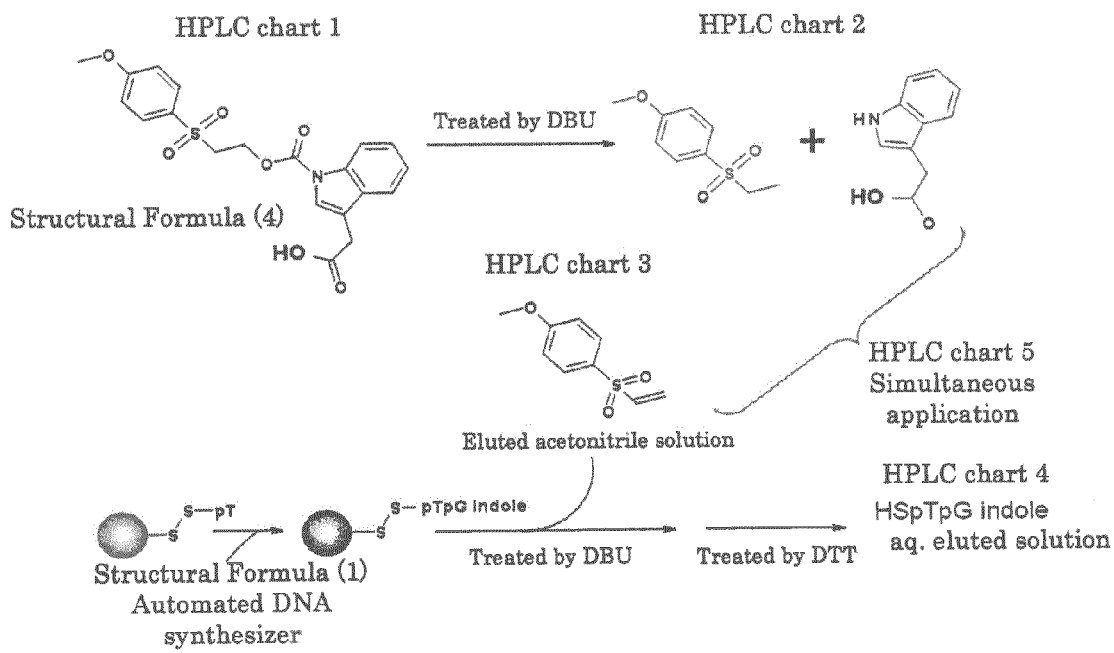
FIG. 13 illustrates a deprotection mechanism of a nucleic acid-synthesizing amidite (having Structural Formula (1)).

As illustrated in FIG. 13, first, HPLC was performed using 20 μL of the compound having Structural Formula (4) (1.2 mM) (HPLC chart 1, FIG. 8). Here, this compound has the same indole group and protecting group as in the nucleic acid-synthesizing amidite obtained in Example 1, and is a precursor of the nucleic acid-synthesizing amidite having Structural Formula (1).

Separately, a mixed solution of the compound having Structural Formula (4) (1.2 mM) and a 20 mM DBU-containing dimethylformamide-acetonitrile (1:99 (by volume)) was left to stand still at room temperature for 15 minutes. Then, HPLC was performed using 20 μL of this reaction mixture (HPLC chart 2, FIG. 9).

H-8-FDNA synthesizer (product of Nihon Techno Service Co., Ltd.) was provided as a DNA synthesizer. Then, a T amidite (product of Glen Research Corp.) and the nucleic acid-synthesizing amidite having Structural Formula (1) were reacted sequentially with a 0.2 μmol S—S bond solid phase resin (product of Glen Research Corp.). Thereafter, a 20 mM DBU-containing acetonitrile solution (5 mL) was applied to the solid-phase resin for 1 hour, and HPLC was performed using 20 μL of the resultant eluate (HPLC chart 3, FIG. 10).

Furthermore, using the above DNA synthesizer, a T amidite (product of Glen Research Corp.) and the nucleic acid-synthesizing amidite having Structural Formula (1) were reacted sequentially with a 0.2 μmol S—S bond solid phase resin (product of Glen Research Corp.). Subsequently, the solid-phase resin was treated with a 20 μM DBU-containing acetonitrile solution and then washed with acetonitrile. Thereafter, 250 μL of 100 mM dithiothreitol (DTT)-containing phosphate buffer (pH 8.3) was applied to the solid-phase resin for 1 hour, and HPLC was performed using 20 μL of the resultant eluate (HPLC chart 4, FIG. 11).

Also, HPLC was performed on the mixed solution giving HPLC chart 3 (114 μL) (i.e., the DBU-treated sample of the nucleic acid-synthesizing amidite having Structural Formula (1)) and the mixed solution giving HPLC chart 2 (5.7 μL) (i.e., the compound having Structural Formula (4)). As a result, the peaks attributed to the mixed solutions were found to be identical (HPLC chart 5, FIG. 12).

These results indicate that, when the nucleic acid-synthesizing amidite having Structural Formula (1) is treated under mild conditions such as DBU treatment in acetonitrile, the protecting group is removed to obtain an indole group-containing nucleic acid.

Notably, the conditions of HPLC analysis in Example 2 are as follows.

[Conditions of HPLC Analysis]

Flow rate: 1 mL/minute

Solution A: 100 mM triethylammonium acetate buffer (pH 7.0)

Solution B: acetonitrile [solution B: 0%→40% (0 minutes→30 minutes)→100% (35 minutes)]

Example 3

A nucleic acid-synthesizing amidite having Structural Formula (1) was synthesized using a protecting group different from that used in Example 1. Specifically, the protecting group used was a group represented by General Formula (I) where R is a phenyl group.

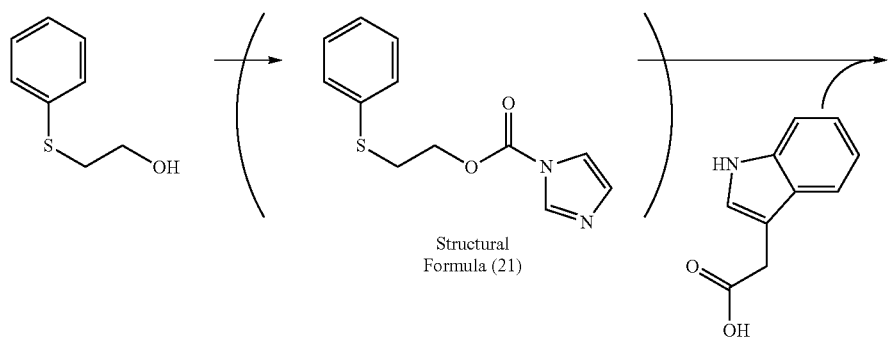

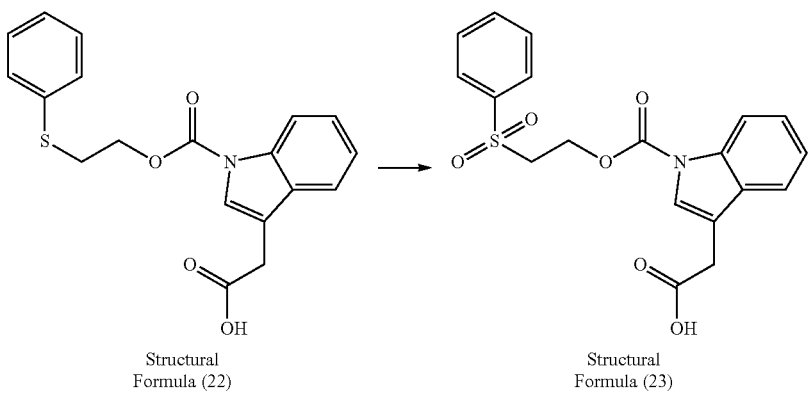

<Synthesis of compound having Structural Formula (21)>
Triphosgene (5.94 g, 20.0 mmol) was dissolved in dehydrated tetrahydrofuran (100 mL), followed by cooling with ice. Subsequently, a mixed solution of 2-(phenylthio)ethanol (8.10 mL, 60.0 mmol), pyridine (5.09 mL, 63.0 mmol) and dehydrated tetrahydrofuran (40 mL) was added dropwise to the cooled solution for about 30 minutes. The resultant mixture was agitated at room temperature for 15 minutes and cooled again with ice. Thereafter, imidazole (4.09 g, 60.0 mmol) and pyridine (5.09 mL, 63.0 mmol) were added to the cooled mixture, followed by agitating at room temperature for 30 minutes. Then, hexane (140 mL) was added to the reaction mixture, followed by agitating and filtrating. The filtrated product was washed with a mixture of tetrahydrofuran and hexane (1:1 (by volume)). The filtrate and washing liquid were concentrated under reduced pressure, to thereby obtain a compound having Structural Formula (21).

3-Indoleacetic acid (9.47 g, 55.0 mmol) was dissolved in dehydrated dimethylformamide (110 mL), and a 60% by mass sodium hydride-oil mixture (4.40 g, 141.6 mmol) was added to the resultant solution, followed by agitating at room temperature for 1 hour and cooling with ice. Subsequently, a solution of a compound having Structural Formula (21) in dehydrated dimethylformamide (30 mL) was added dropwise thereto, and the resultant mixture was agitated for 5 minutes and then at room temperature for 30 minutes. Thereafter, ammonium chloride (10 g) was added to the reaction mixture, and the resultant mixture was concentrated under reduced pressure. The residue was dissolved in ethyl acetate and washed with water. The ethyl acetate solution was concentrated under reduced pressure. The residue was purified by medium pressure chromatography (1% acetic acid (constant), ethyl acetate:hexane=1:2→1:1 (by volume)), to thereby obtain 12.80 g (36.03 mmol) of a compound having Structural Formula (22).

<Synthesis of compound having Structural Formula (23)>
The compound having Structural Formula (22) (11.39 g, 32.05 mmol) was dissolved in dichloromethane (80 mL). Under cooling with ice, 16.22 g of 70% m-chloroperoxybenzoic acid in water was added to the resultant solution, followed by agitating for 30 minutes. The reaction solution was washed with water, and the dichloromethane solution was concentrated under reduced pressure. The residue was purified by medium pressure chromatography (2% acetic acid (constant), dichloromethane ethyl acetate=1:0→4:1 (by volume)), to thereby obtain 10.07 g (25.98 mmol, 81%) of a compound having Structural Formula (23).

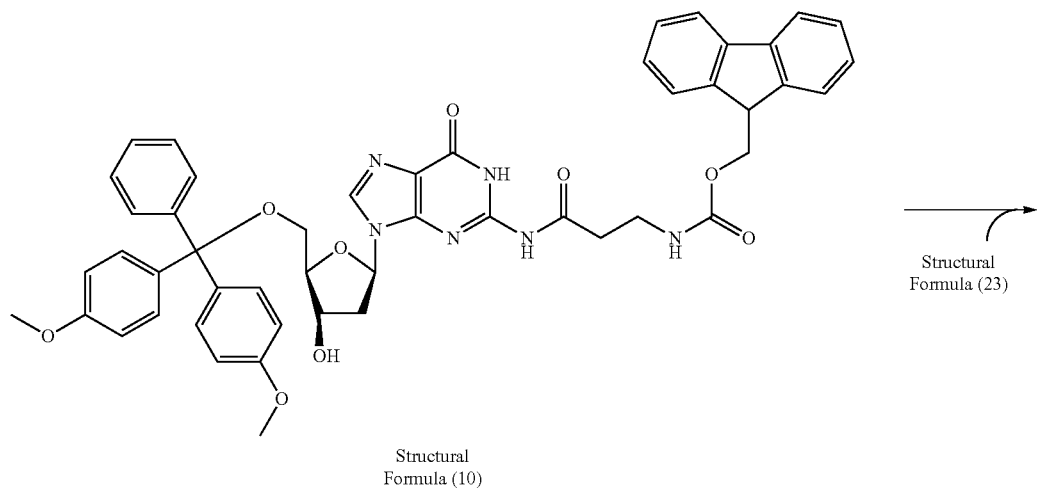
Structural Formula (10)
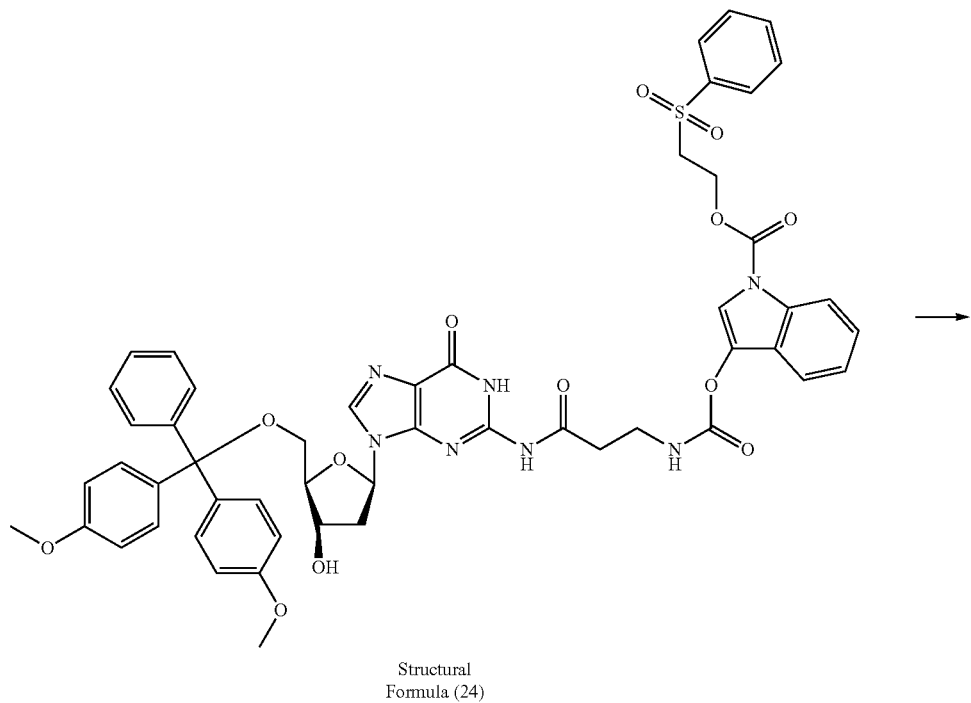
Structural Formula (24)

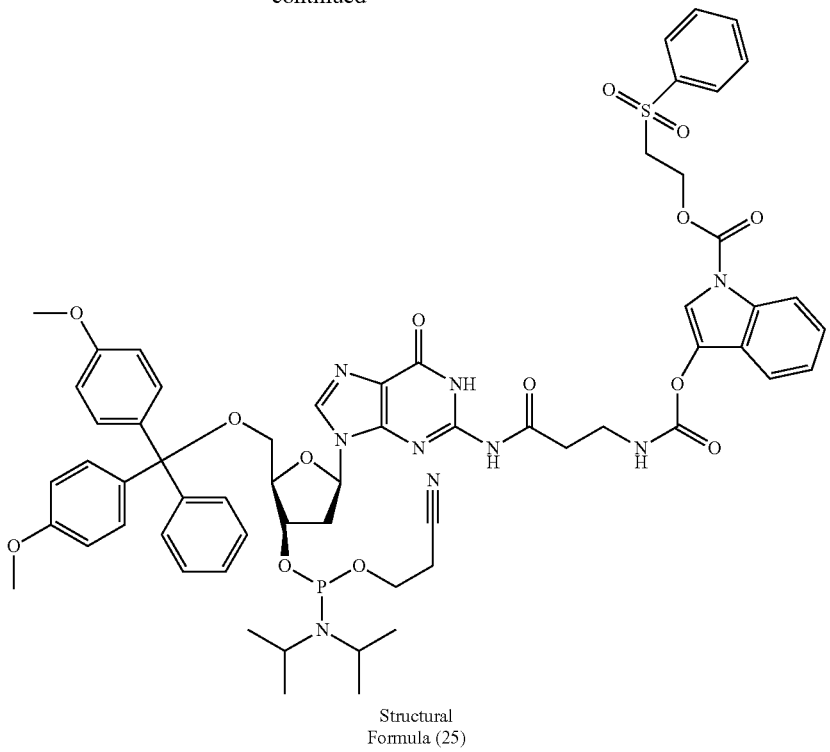 [SMILES: COc1ccc(C(OC[C@H]2O[C@@H](n3cnc4c(=O)[nH]c(NC(=O)CCNC(=O)Oc5cn(C(=O)OCCS(=O)(=O)c6ccccc6)c6ccccc56)nc43)C[C@H]2OP(OCCC#N)N(C(C)C)C(C)C)(c2ccccc2)c2ccc(OC)cc2)cc1]

Structural Formula (25)

<Synthesis of compound having Structural Formula (24)>
The compound having Structural Formula (10) (17.26 g, 20.0 mmol) was dissolved in dehydrated dichloromethane (40 mL), and triethylsilane (4.79 mL, 30.0 mmol) and diazabicycloundecene (4.49 mL, 30.0 mmol) were added to the resultant solution, followed by agitating at room temperature for 10 minutes. Subsequently, triethylamine hydrochloride (4.96 g, 36.0 mmol) was added to the resultant mixture, followed by agitating for 5 minutes, to thereby obtain solution A.

The compound having Structural Formula (23) (7.75 g, 20.0 mmol) was dissolved in dehydrated dimethoxyethane, and the resultant solution was concentrated under reduced pressure three times. The residue was suspended in dehydrated dichloromethane (60 mL). Subsequently, diisopropylethylamine (4.09 mL, 23.47 mmol) and O-benzotriazolyl-N,N,N',N'-tetramethyluronium hexafluorophosphate (7.97 g, 21.0 mmol) were added to the suspension, followed by agitating at room temperature for 30 minutes. The resultant solution was added to the above-prepared solution A, and the mixture was agitated at room temperature for 30 minutes. The reaction solution was washed with water, and the dichloromethane solution was concentrated under reduced pressure. The residue was purified by medium pressure chromatography (ethyl acetate ethanol=19:1→9:1 (by volume)), to thereby obtain 13.28 g (13.15 mmol, 66%) of a compound having Structural Formula (24).

<Synthesis of compound having Structural Formula (25)>
The compound having Structural Formula (24) (13.28 g, 13.15 mmol) was added to a solvent mixture of dehydrated acetonitrile and dehydrated dichloromethane, and the resultant solution was concentrated under reduced pressure three times. The residue was dissolved in dehydrated dichloromethane (40 mL). Under cooling with ice, dimethylaminopyridine (80 mg, 0.66 mmol) and diisopropylethylamine (2.60 mL, 15.78 mmol) were added to the resultant solution, and a solution of 2-cyanoethyldiisopropylchlorophosphoroamidite (3.26 mL, 14.47 mmol) in methylene chloride (13 mL) was added dropwise to the mixture for 5 minutes or longer. The thus-obtained mixed solution was agitated under cooling with ice for 5 minutes and left to stand still at 4° C. overnight. Then, methanol (3.0 mL) was added to the mixture, followed by agitating for 30 minutes. The reaction solution was washed with water, and the dichloromethane solution was concentrated under reduced pressure. The residue was purified by medium pressure chromatography (2% pyridine-containing ethyl acetate-hexane (2:1 (by volume)): 2% pyridine and 7% ethanol-containing ethyl acetate=1: 0→0:1 (by volume)), to thereby obtain 4.86 g (30%) of a compound having Structural Formula (25). However, the compound was found to contain a small amount of impurities (possibly decomposed products), and the yield obtained using a DNA synthesizer was found to be 95% or lower.

In Comparative Examples 1 to 3, the groups having the following Structural Formulas (201) to (203) were used as protecting groups for the syntheses of amidites.

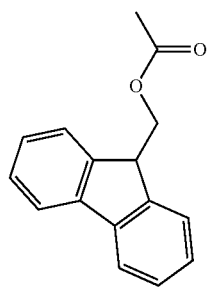

(201)

(202)

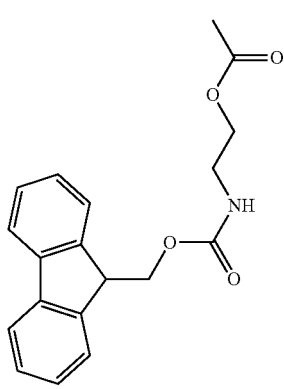

(203)

Comparative Example 1

Using the protecting group having Structural Formula (201), an amidite was synthesized as follows.

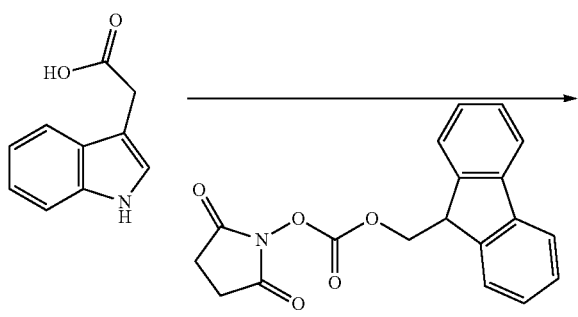

FMOCOSu

Structural Formula (26)

<Synthesis of compound having Structural Formula (26)>
3-Indoleacetic acid (0.96 g, 5.5 mmol) was dissolved in dehydrated dimethylformamide (11 mL). Subsequently, a 60% by mass sodium hydride-oil mixture (440 mg, 5.5 mmol) was added to the resultant solution, followed by agitating at room temperature for 1 hour and cooling with ice. Thereafter, a solution of FMOCOSu (2.02 g, 6 mmol) in dehydrated dimethylformamide (3 mL) was added to the cooled mixture, followed by agitating for 5 minutes and then at room temperature for 30 minutes. Subsequently, ammonium chloride (13.8 g) was added to the reaction mixture, and the mixture was concentrated under reduced pressure. The residue was dissolved in ethyl acetate, and the resultant solution was washed with water. However, the ethyl acetate solution was found to contain no compound having Structural Formula (26); i.e., to be a mixture of various other compounds.

Comparative Example 2

Using the protecting group having Structural Formula (202), an amidite was synthesized as follows.

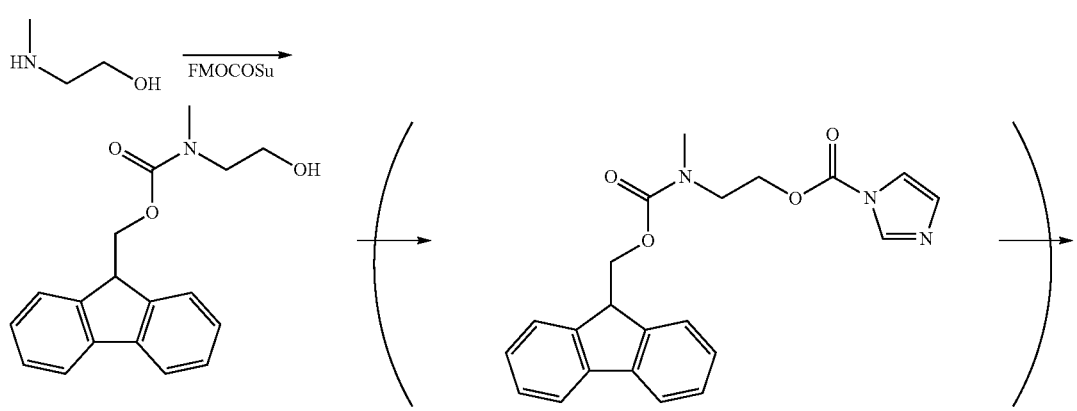

Structural Formula (27)  Structural Formula (28)

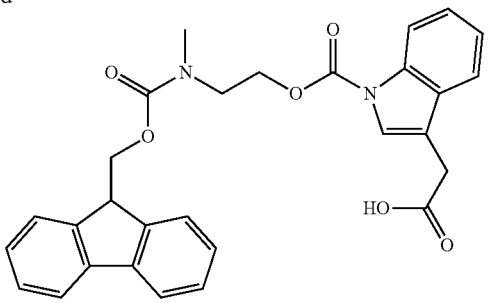

Structural Formula (29)

<Synthesis of compound having Structural Formula (27)>
FMOCOSu (33.74 g, 100 mmol) was dissolved in dichloromethane (100 mL). Under cooling with ice, 2-(methylamino)ethanol (8.25 mL, 105 mmol) was added to the resultant solution, followed by agitating at room temperature overnight. The reaction solution was washed with water, and the dichloromethane solution was concentrated under reduced pressure. The residue was purified by medium pressure chromatography (ethyl acetate:hexane=1:1→1:0 (by volume)), to thereby obtain 28.72 g (97%) of a compound having Structural Formula (27).

<Synthesis of compound having Structural Formula (29)>
Triphosgene (5.94 g, 20.0 mmol) was dissolved in dehydrated tetrahydrofuran (100 mL), the resultant solution was cooled with ice. Subsequently, a mixed solution of the compound having Structural Formula (27) (17.84 g, 60.0 mmol), pyridine (5.09 mL, 63.0 mmol) and dehydrated tetrahydrofuran (40 mL) was added dropwise to the cooled mixture for about 30 minutes, followed by agitating at room temperature for 15 minutes and then cooling again with ice. Thereafter, imidazole (4.09 g, 60.0 mmol) and pyridine (5.09 mL, 63.0 mmol) were added thereto, followed by agitating at room temperature for 30 minutes. Then, hexane (140 mL) was added to the reaction mixture, followed by filtrating. The filtrated product was washed with a mixture of tetrahydrofuran and hexane (1:1 (by volume)). The filtrate and washing liquid were concentrated under reduced pressure, to thereby obtain a compound having Structural Formula (28).

3-Indoleacetic acid (9.47 g, 55.0 mmol) was dissolved in dehydrated dimethylformamide (110 mL). Subsequently, a 60% by mass sodium hydride-oil mixture (4.40 g, 141.6 mmol) was added to the resultant solution, followed by agitating at room temperature for 1 hour and cooling with ice. Subsequently, a solution of the compound having Structural Formula (28) in dehydrated dimethylformamide (30 mL) was added dropwise thereto, and the resultant mixture was agitated for 5 minutes and then at room temperature for 30 minutes. Thereafter, ammonium chloride (10 g) was added to the reaction mixture, and the resultant mixture was concentrated under reduced pressure. The residue was dissolved in ethyl acetate and washed with water. The ethyl acetate solution was concentrated under reduced pressure. However, the ethyl acetate solution was found to contain no compound having Structural Formula (29); i.e., to be a mixture of various other compounds.

Comparative Example 3

Using the protecting group having Structural Formula (203), an amidite was synthesized as follows.

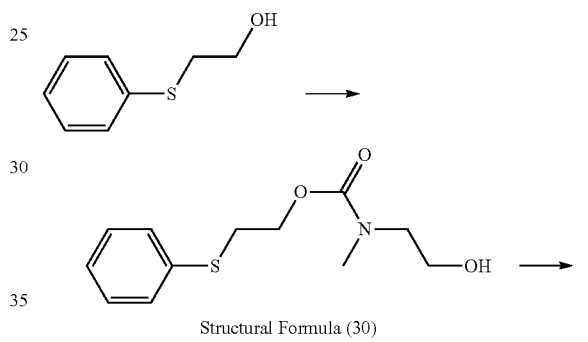

Structural Formula (30)

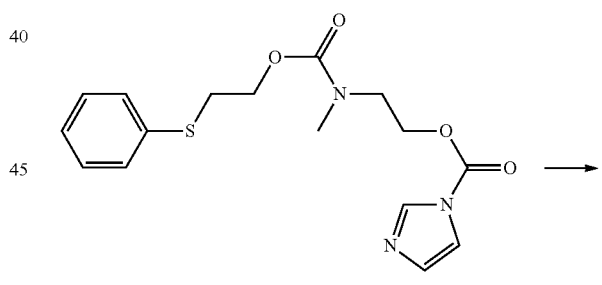

Structural Formula (31)

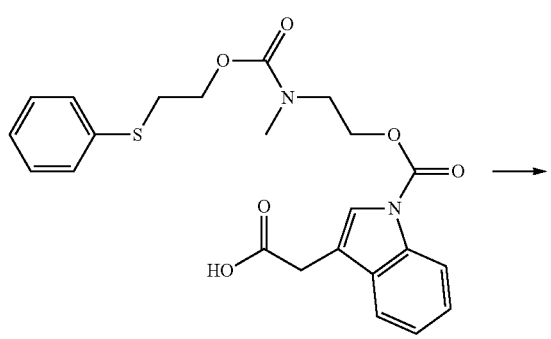

Structural Formula (32)

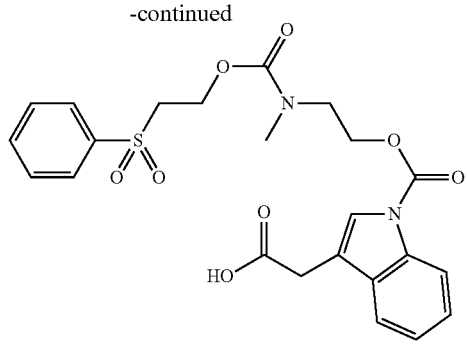

Structural Formula (33)

<Synthesis of compound having Structural Formula (30)>
Triphosgene (5.94 g, 20.0 mmol) was dissolved in dehydrated tetrahydrofuran (100 mL), followed by cooling with ice. Subsequently, a mixed solution of 2-(phenylthio)ethanol (8.10 mL, 60.0 mmol), pyridine (5.09 mL, 63.0 mmol) and dehydrated tetrahydrofuran (40 mL) was added dropwise to the cooled solution for about 30 minutes. The resultant mixture was agitated at room temperature for 15 minutes and cooled again with ice. Thereafter, a mixture of N-hydroxysuccinimide (7.25 g, 63.0 mmol) and pyridine (5.09 mL, 63.0 mmol) in tetrahydrofuran (30 mL) was added thereto, the resultant mixture was agitated at room temperature for 30 minutes. Then, hexane (140 mL) was added to the reaction mixture, followed by filtrating. The filtrated product was washed with tetrahydrofuran-hexane (1:1 (by volume)). The filtrate and washing liquid were concentrated under reduced pressure. The residue was dissolved in dichloromethane (50 mL). Under cooling with ice, 2-(methylamino)ethanol (5.28 mL, 66.0 mmol) was added to the resultant solution, followed by agitating at room temperature for 2 hours. The reaction solution was washed with water, and the dichloromethane solution was concentrated under reduced pressure. The residue was purified by medium pressure chromatography (ethyl acetate:hexane=1:1→1:0 (by volume)), to thereby obtain 14.19 g (93%) of a compound having Structural Formula (30).

<Synthesis of compound having Structural Formula (31)>
Triphosgene (5.50 g, 18.52 mmol) was dissolved in dehydrated tetrahydrofuran (93 mL), followed by cooling with ice. Subsequently, a mixed solution of the compound having Structural Formula (30) (14.19 g, 55.6 mmol), pyridine (4.71 mL, 58.3 mol) and dehydrated tetrahydrofuran (37 mL) was added dropwise to the cooled mixture for about 30 minutes, followed by agitating at room temperature for 15 minutes and then cooling again with ice. Thereafter, imidazole (3.79 g, 55.6 mmol) and pyridine (4.71 mL, 58.3 mmol) were added thereto, and the resultant mixture was agitated at room temperature for 30 minutes. Then, hexane (120 mL) was added to the reaction mixture, followed by filtrating. The filtrated product was washed with tetrahydrofuran-hexane (1:1 (by volume)). The filtrate and washing liquid were concentrated under reduced pressure, to thereby obtain a compound having Structural Formula (31).

3-Indoleacetic acid (8.78 g, 51.0 mmol) was dissolved in dehydrated dimethylformamide (100 mL). Subsequently, a 60% by mass sodium hydride-oil mixture (4.08 g, 131 mmol) was added to the resultant solution, followed by agitating at room temperature for 1 hour and cooling with ice. Subsequently, a solution of the compound having Structural Formula (31) in dehydrated dimethylformamide (30 mL) was added dropwise thereto, and the resultant mixture was agitated for 5 minutes and then at room temperature for 30 minutes. Thereafter, ammonium chloride (10 g) was added to the reaction mixture, and the resultant mixture was concentrated under reduced pressure. The residue was dissolved in ethyl acetate and washed with water. The ethyl acetate solution was concentrated under reduced pressure. The residue was purified by medium pressure chromatography (1% acetic acid (constant), ethyl acetate:hexane=1:2→2:1 (by volume)), to thereby obtain 14.03 g (30.7 mmol) of a compound having Structural Formula (32).

<Synthesis of compound having Structural Formula (33)>
The compound having Structural Formula (32) (10.66 g, 23.34 mmol) was dissolved in dichloromethane (60 mL). Under cooling with ice, 11.82 g of 70% m-chloroperoxybenzoic acid in water was added to the resultant solution, followed by agitating for 30 minutes. The insoluble matter was removed through filtration, and the reaction solution was washed with water. The dichloromethane solution was concentrated under reduced pressure. The residue was purified by medium pressure chromatography (2% acetic acid (constant), dichloromethane ethyl acetate=1:0→2:1 (by volume)), to thereby obtain 9.98 g (20.42 mmol, 87%) of a compound having Structural Formula (33).

<Evaluation on deprotection of the compound having Structural Formula (33)> The compound having Structural Formula (33) was dissolved in dimethylformamide. Then, a mixture containing the compound having Structural Formula (33) (1.2 mM) and 20 mM DBU-containing dimethylformamide (1%)-acetonitrile was left to stand still at room temperature for 15 minutes. But, a considerable amount of the compound having Structural Formula (33) remained unchanged. Also, it could be confirmed through TLC that a small amount of 3-indoleacetic acid was produced, indicating that it was difficult to completely remove the protecting group under the above conditions.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification related to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A nucleic acid-synthesizing amidite represented by the following General Formula (II):

General Formula (II)

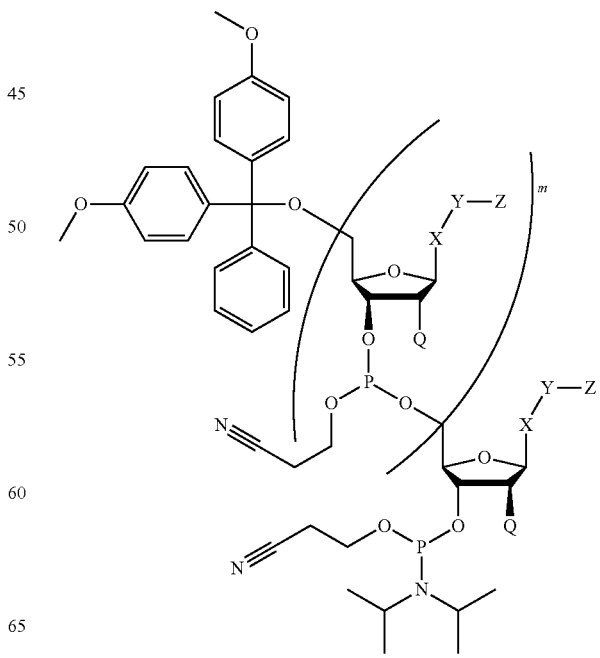

where:
X represents a nucleic acid base which may have a substituent;
Y represents an indole group;
Z represents a protecting group for the 1-nitrogen atom of the indole group;
Q represents a hydrogen atom or a hydroxyl group; and
m is 0 or 1;
wherein:
the protecting group Z is capable of being removed from the 1-nitrogen atom of the indole group Y in an aprotic solvent; and
the protecting group Z is a sulfonylethyl carbamate group represented by the following General Formula (I):

General Formula (I)

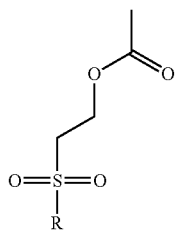

where R represents an alkyl group, a substituted alkyl group, a phenyl group, or a substituted phenyl group.

2. The nucleic acid-synthesizing amidite according to claim 1, wherein the nucleic acid base X in General Formula (II) is adeninyl, guaninyl or cytosinyl.

3. The nucleic acid-synthesizing amidite according to claim 1, further comprising a protecting group for the phosphoric acid group in General Formula (II), the protecting group being selected from the group consisting of a cyanoethyl group, a substituted cyanoethyl group, a fluorenylmethyl group, a substituted fluorenylmethyl group, a p-nitrophenethyl group, a substituted p-nitrophenethyl group, a nitroethyl group, and a substituted nitroethyl group.

4. The nucleic acid-synthesizing amidite according to claim 1, having a structure expressed by the following Structural Formula (I):

5. A nucleic acid-synthesizing method comprising:
synthesizing a nucleic acid with a nucleic acid-synthesizing amidite which comprises an indole group whose 1-nitrogen atom is protected by a protecting group capable of being removed from the 1-nitrogen atom of the indole group in an aprotic solvent and is represented by General Formula (II):

General Formula (II)

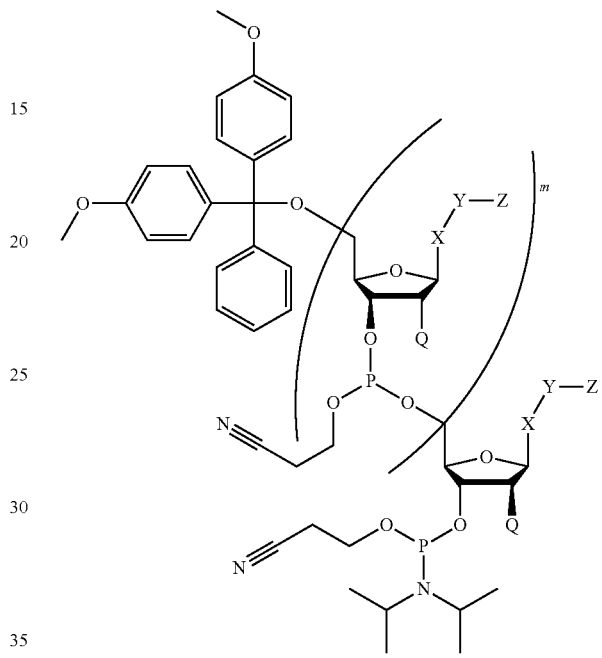

where X represents a nucleic acid base which may have a substituent, Y represents the indole group, Z represents the protecting group for the 1-nitrogen atom of the indole group, Q represents a hydrogen atom or a hydroxyl group, and m is 0 or 1.

6. The nucleic acid-synthesizing method according to claim 5, wherein the synthesizing comprises subjecting the Structural Formula (1)

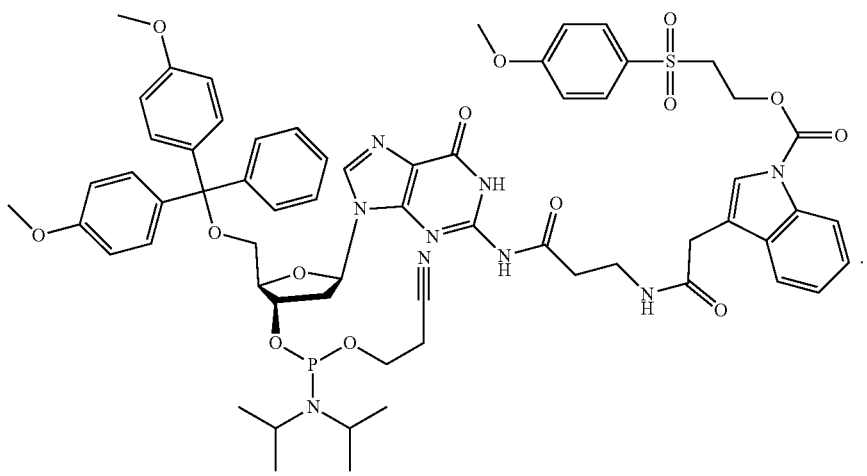

nucleic acid-synthesizing amidite and a nucleoside compound to a condensation reaction.

7. The nucleic acid-synthesizing method according to claim 5, wherein the synthesizing further comprises removing the protecting groups of the nucleic acid-synthesizing amidite in the aprotic solvent after the condensation reaction.

8. The nucleic acid-synthesizing method according to claim 5, wherein the aprotic solvent is at least one selected from the group consisting of acetonitrile, dichloromethane, N,N-dimethylformamide and N-methylpyrrolidone.

9. The nucleic acid-synthesizing method according to claim 5, wherein the aprotic solvent comprises a bulky base therein, and the protecting groups are capable of being removed from the nucleic acid-synthesizing amidite within 15 minutes by the bulky base.

10. The nucleic acid-synthesizing method according to claim 9, wherein the bulky base is at least one selected from the group consisting of 1,8-diazabicyclo[5.4.0]-7-undecene, 1,5-diazabicyclo[4.3.0]-5-nonene and tetramethyl guanidine.

* * * * *